(12) United States Patent
Byron et al.

(10) Patent No.: US 9,140,689 B2
(45) Date of Patent: Sep. 22, 2015

(54) METHODS OF DETERMINING SUSCEPTIBILITY OF TUMORS TO TYROSINE KINASE INHIBITORS

(75) Inventors: Sara Ann Byron, Phoenix, AZ (US); Pamela Michelle Pollock, Queensland (AU)

(73) Assignees: Translational Genomics Research Institute, Phoenix, AZ (US); Queensland University of Technology, Queensland (AU)

(*) Notice: Subject to any disclaimer, the term of this patent is extended or adjusted under 35 U.S.C. 154(b) by 1192 days.

(21) Appl. No.: 13/047,769

(22) Filed: Mar. 14, 2011

(65) Prior Publication Data

US 2011/0275084 A1 Nov. 10, 2011

Related U.S. Application Data

(60) Provisional application No. 61/313,762, filed on Mar. 14, 2010.

(51) Int. Cl.
  *C12Q 1/68* (2006.01)
  *G01N 33/50* (2006.01)
  *C07K 14/705* (2006.01)

(52) U.S. Cl.
  CPC ...... *G01N 33/5011* (2013.01); *C07K 14/70503* (2013.01); *G01N 2333/71* (2013.01); *G01N 2800/52* (2013.01)

(58) Field of Classification Search
  None
  See application file for complete search history.

(56) References Cited

FOREIGN PATENT DOCUMENTS

WO  WO 2008118877 A2 * 10/2008
WO  WO 2008118877     12/2008

OTHER PUBLICATIONS

Pollock et al. (Frequent activating FGFR2 mutations in endometrial carcinomas parallel germline mutations associated with craniosynostosis and skeletal dysplasia syndromes, Oncogene (2007) 26, 7158-7162, May 21, 2007).*
Byron et al. (Inhibition of Activated Fibroblast Growth Factor Receptor 2 in Endometrial Cancer Cells Induces Cell Death Despite PTEN Abrogation, Cancer Res 2008; 68: (17). Sep. 1, 2008).*
Byron et al. (FGFR2 as a molecular target in endometrial cancer, Future Oneol. (20(9) 5(1), 27-32, Feb. 2009).*
Cha et al. (Aberrant receptor internalization and enhanced FRS2-dependent signaling contribute to the transforming activity of the fibroblast growth factor receptor 2 IIIb C3 isoform, J Biol Chem. Mar 6, 2009;284(10):6227-40, Dec. 22, 2008).*
Chen et al. (A 'Molecular Brake' in the Kinase Hinge Region Regulates the Activity of Receptor Tyrosine Kinases, Mol Cell. Sep. 7, 2007; 27(5): 717-730, Nov. 26, 2007).*
European Search Report for Application serial No. 11756822.0 dated Sep. 19, 2013.
Byron S A et al "FGFR2 as a molecular target in Endomtrial cancer" Future Oncology, Future Medicine LTD., London GB vol. 5 No. 1 pp. 27-32 Jan. 1, 2009.
Chen Huaibin et al "A molecular break in the kinasa hinge region regulates the activity of receptor tyrosine kinases" Molecular Cell vol. 27 No. 5 pp. 717-730 Sep. 7, 2007.
Katoh Masaru "Cancer genomics and genetics of FGFR2 (review)" International Journal of Oncology vol. 33 No. 2 pp. 233-237 Aug. 2008
International Preliminary Report on Patentability for PCT application No. PCT/US2011/028415 dated Sep. 18, 2012.
International Search Report and Written Opinion of Searching Authority for PCT application No. PCT/US2011/028415 dated May 25, 2011.
Blencke et al. Characterization of a conserved structural determinant controlling protein kinase sensitvity to selective inhibitors. Chem Biol May 2004 vol. 11 No. 5 pp. 691-701.
NCBI NP_075259.2 Fibroblast growth factor receptor 2 isoform 2 precursor [*Homo sapiens*] [online] May 22, 2008. Available on the internet: http://www.ncbi.nlm.nih.gov/protein/NP_075259.2.
NCBI NP_075598.2 Basic Fibroblast growth factor receptor 1 isoform 1 precursor [*Homo sapiens*] [online] Dec. 13, 2009. Available on the internet: http://www.ncbi.nlm.nih.gov/protein/NP_075598.2.
Pollock et al, Frequent activating FGFR2 mutations in endometrial carcinomas parallel gerrnline mutations associated with craniosynostosis and skeletal dysplasia syndromes. Oncogene Nov. 1, 2007 vol. 26 No. 50 pp. 7158-7162.
Katoh et al FGFR2-related pathogenesis and FGFR2-targeted therapeutics (Review). Interant. J. Mol. Med. Mar. 2009 vol. 23 No. 3 pp. 307-311.

* cited by examiner

*Primary Examiner* — Stephanie K Mummert
*Assistant Examiner* — Aaron Priest
(74) *Attorney, Agent, or Firm* — The Noblitt Group, PLLC

(57) ABSTRACT

This disclosure provides tyrosine kinase protein and nucleic acid variants, particularly FGFR2 variants, which are linked to drug resistance. The disclosure further provides methods of diagnosis and theranosis, and development of new therapeutic agents using these molecules and fragments thereof, and kits for employing these methods and compositions.

10 Claims, 5 Drawing Sheets

METHODS OF DETERMINING SUSCEPTIBILITY OF TUMORS TO TYROSINE KINASE INHIBITORS

CROSS-REFERENCE TO RELATED APPLICATIONS

This application claims the priority of U.S. provisional applications entitled METHODS OF DETERMINING SUSCEPTIBILITY OF TUMORS TO TYROSINE KINASE INHIBITORS, with application No. 61/313,762, filed on Mar. 14, 2010, which is hereby incorporated by reference in its entirety.

FIELD OF THE INVENTION

This invention relates to tyrosine kinases, specifically receptor tyrosine kinases with one or more variants. Further, it relates to methods of using these variants in screens and analyses, including diagnoses, theranoses, and systems for identification susceptibility of tumors to tyrosine inhibitor and/or screening of pharmaceutical compounds.

BACKGROUND OF THE INVENTION

Endometrial cancer includes all forms and subtypes of the disease, including for example, serous, mucinous, and endometrioid histological subtypes or any other cancer that starts in the endometrium, which includes the lining of the uterus. Particularly, cancer of the endometrium is the most common gynecologic malignancy and accounts for 6% of all cancers in women.

Members of the fibroblast growth factor receptor (FGFR) tyrosine kinase family have been shown to be amplified or mutationally activated in endometrial cancer and a variety of other cancer types, including breast cancer, ovarian cancer, lung cancer, gastric cancer, bladder cancer, glioblastoma and rhabdomyosarcoma, making FGFRs an attractive potential therapeutic target. Targeted tyrosine kinase inhibitors (TKIs) have shown success in cancer treatment. However, the long-term efficacy of these TKIs is frequently limited by development of resistance to the TKIs. The resistance developed to TKIs can be due to mutation of the target kinase. Therefore, there is a need to determine specific resistance profiles for each particular compound by discovering relevant mutation(s) in FGFR. Such FGFR mutation(s) can be used to develop a companion test of a drug, i.e., screening for susceptibility to a FGFR inhibitor. The identification of specific TKI-resistant FGFR mutations is also required to develop second generation inhibitors, whether it is an FGFR-specific inhibitor, or a multi-targeted protein kinase inhibitor, or a combination of selective antagonists, as in an anti-tumor or anti-cancer drug.

SUMMARY OF THE INVENTION

Briefly, therefore, one aspect of the present invention provides a method for identifying a tumor cell from a sample as resistant to an inhibitor of fibroblast growth factor receptor 2 (FGFR2) to induce tumor cell death, inhibit tumor growth, or decrease risk of metastasis of a tumor cell. The method comprises (1) receiving a sample; and (2) detecting the presence of at least one FGFR2 mutation variant chosen from M536I, M538I, I548V, N550H, N550K, N550S, V565I, E566G, L618M, Y770IfsX14 in the sample from the subject. In this method, the presence of at least one of the FGFR2 variants indicates that the subject is resistant to the inhibitor.

Another aspect of the present invention provides a method for identifying an agent that induces tumor cell death, inhibits tumor growth, or decreases risk of metastasis of a tumor cell. The method comprises (1) contacting the tumor cell with the agent, wherein the tumor cell comprises at least one FGFR2 mutation variant chosen from M536I, M538I, I548V, N550H, N550K, N550S, V565I, E566G, L618M, Y770IfsX14; and, (2) testing one or more tumor cell responses to the agent. The tumor cell response that may be tested may be chosen from tyrosine kinase activity, tumor cell count, metastasis, and apoptosis, wherein a lower level of tyrosine kinase activity, tumor cell count, or metastasis indicates that the agent is an inhibitor to the FGFR2 variant; wherein the tumor cell response is determined via comparison and relative to a control sample.

Yet another aspect of the present invention provides a kit for facilitating the administration of a pharmaceutical composition to induce tumor cell death, inhibit tumor growth, or decrease risk of metastasis of a tumor cell and determination of response thereto, comprising: one or more reagents for detecting at least one FGFR2 variant chosen from M536I, M538I, I548V, N550H, N550K, N550S, V565I, E566G, L618M, Y770IfsX14.

Other aspects and iterations of the invention are described in more detail below.

DETAILED DESCRIPTION OF THE INVENTION

Figure 1:
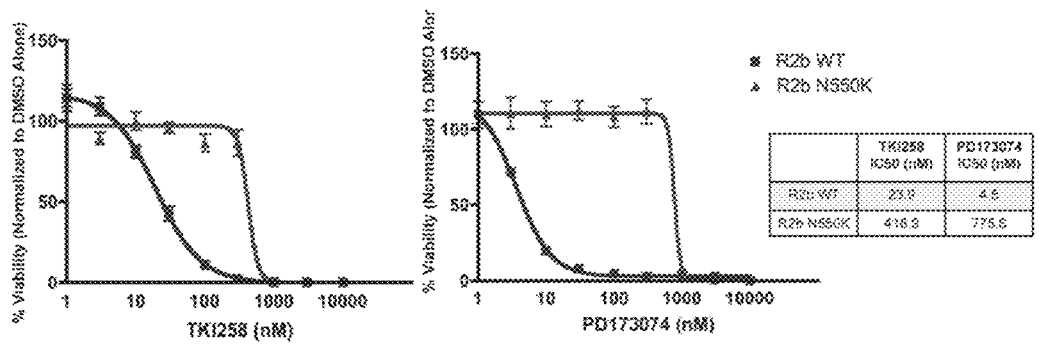
FIG. 1 depicts the $IC_{50}$ graphs of TKI258 and PD173074 in BaF3/FGFR2b wildtype and N550K cells.

The present invention provides a panel of FGFR2 mutation variants, and more specifically, methods and kits for identifying inhibitor susceptible or resistance tumor cells, and a method for screening agents that induce tumor cell death, inhibit tumor growth, or decrease risk of metastasis of a tumor cell, comprising a particular FGFR2 mutation variant disclosed herein.

Receptor tyrosine kinases (RTK)s are the high-affinity cell surface receptors for many polypeptide growth factors, cytokines, and hormones. Of the 90 unique tyrosine kinase genes identified in the human genome, 58 encode receptor tyrosine kinase proteins. There are mainly 5 families of RTKs: epidermal growth factor receptor (EGFR) family; fibroblast growth factor receptor (FGFR) family; vascular endothelial growth factor receptor (VEGFR) family; RET receptor family; and, Eph receptor family. RTKs have been shown not only to be key regulators of normal cellular processes but also to have a critical role in the development and progression of many types of cancer.

I. Fibroblast Growth Gactor Receptors (FGFRs)

Fibroblast growth factors (FGFs) acting through their cognate receptors (FGFRs) play vital roles in development and de-regulation of FGF/FGFR signalling is associated with many developmental syndromes. FGF/FGFR signalling is important in tumour angiogenesis and FGFRs drive oncogenes in certain cancers and act in a cell autonomous fashion to maintain the malignant properties of tumour cells. Members of the fibroblast growth factor receptor (FGFR) tyrosine kinase family have been shown to be amplified or mutationally activated in a variety of cancer types, including breast, endometrial, ovarian, lung, gastric, and bladder cancers, as well as glioblastoma and rhabdomyosarcoma, making FGFRs an attractive potential therapeutic target.

The FGFRs consist of an extracellular ligand domain composed of three immunoglobulin-like domains, a single transmembrane helix domain, and an intracellular domain with tyrosine kinase activity. The natural alternate splicing of four FGFR genes, FGFR1, FGFR2, FGFR3, and FGFR4, results in the production of over 48 different isoforms of FGFR, with FGFR2b being one of them. FGFR isoforms vary in their extracellular region and ligand-binding properties but all share a common and kinase domains.

It has been observed that the activation of wild-type (WT) FGFR, or the subsequent acquisition of activating mutations of FGFR is associated with cancer progression, and impacts drug response and/or resistance, chemotherapy response and/or resistance, and survival rate.

A. FGFR2

The concept of the FGFR2 gene encompasses a gene of human origin with a coding nucleotide sequence set forth in SEQ ID NO:1, or homologs including allelic variants and orthologs. The FGFR2 protein encompasses a protein, also preferably of human origin, having the amino acid sequence set forth in SEQ ID NO:2 or homologs, including orthologs thereof.

FGFR2 belongs to a family of structurally related tyrosine kinase receptors (FGFRs 1-4) encoded by four different genes. FGFR2 is a glycoprotein composed of three extracellular immunoglobulin-like (Ig) domains, a transmembrane domain, and a split tyrosine kinase domain. Alternative splicing in the IgIII domain is a primary determinant of both the patterns of redundancy and specificity in FGF/FGFR binding and signaling. This splicing event is tissue specific and gives rise to the IIIb and IIIc receptor isoforms for FGFR1 and FGFR3, which possess distinct ligand specificities. For FGFR2, cells of an epithelial linage only express the "IIIb" isoform encoded by exon 8 (FGFR2b; SEQ ID NO:2; NP_075259.2), while mesenchymally derived cells exclusively express the "IIIc" isoform utilizing exon 9 (FGFR2c; SEQ ID NO:3; NP_000132.1). The FGFR2b isoform predominantly binds FGF1, FGF3, FGF7 and FGF10, while FGFR2c does not bind FGF7 and FGF10 but does bind FGF1, FGF2, FGF4, FGF6, and FGF8 with high affinity.

A mutation in FGFR2 that causes increased activity of FGFR2 in a test subject or a biological sample may also be called an activation mutation. Activation mutations display higher total FGFR2 activity in the test subject or biological sample in comparison with a control, e.g., a healthy subject or a standard sample. Therefore, the activity of FGFR2 in a healthy subject or a standard sample is 5%, 10%, 20%, 30%, 40%, 50%, 60%, 70%, 80%, 90%, 95%, 99% relative to that in a subject or a sample carrying activation mutation in FGFR2. The increased activity of FGFR2 in a subject or a sample carrying activation mutation may result from, for example, increased basal FGFR2 activity, prolonged stimulation, delayed degradation, or over-expression, e.g., due to enhanced ligand binding, promiscuous or inappropriate ligand binding, constitutive receptor dimerization, impaired recycling resulting in augmentation of signaling, delayed degradation, or kinase activation.

A higher expression level of FGFR2 may result from, for example, a mutation in a non-coding region of a FGFR2 gene or a mutation in a coding or non-coding gene involved in FGFR2 transcription or translation. The expression level of FGFR2 can be determined, for example, by comparing FGFR2 mRNA or the level of FGFR2 protein in a test subject as compared to a control, for example, by comparing the tumor to normal endometrium (e.g., a normal adjacent endometrium sample).

Conserved variants encompass any mutation or other variant in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Depending on the location of the mutation in the overall context of the protein, some substitution may have little or no effect on the apparent molecular weight or isoelectric point of the protein or polypeptide. However some conserved variants have been found to alter protein conformation and function, including several variants discovered and disclosed herein.

Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. The concept of a variant further encompasses a polypeptide or enzyme which has at least 60%, 75%, 85%, 90%, or 95%, amino acid identity as determined by algorithms such as BLAST or FASTA and which has the same or substantially similar properties and/or activities as the native or parent protein or enzyme to which it is compared.

One example of such a variant is a gain-of-function variant. Gain-of-function variants of polypeptides encompass any variant in which a change in one or more amino acid residues in a protein or enzyme improves the activity of the polypeptide. Examples of activities of a polypeptide that may be improved by a change resulting in a gain of function variant include but are not limited to enzymatic activity, binding affinity, phosphorylation or dephosphorylation efficiency, activation, deactivation, or any other activity or property of a protein that may be quantitatively measured by some method now known or yet to be disclosed.

Proteins that possess a common evolutionary origin may be homologous or similar to one another. Examples of homologous or similar proteins include proteins from superfamilies (e.g., the immunoglobulin superfamily) and homologous proteins from different species. Such proteins and their encoding genes have sequence homology with one another. The homology may be expressed in terms of percent similarity or the presence of specific residues or motifs at conserved positions.

A mutation may be any detectable change in genetic material such as DNA, or a corresponding change in the RNA or protein product of that genetic material. A mutant may be any biological material in which one or more mutations are detected when compared to a control material. Examples of mutations include gene mutations, in which the DNA sequence of a gene or any controlling elements surrounding the gene is altered. Controlling elements include promoter, enhancer, suppressor or silencing elements capable of controlling a given gene. Other examples of mutations include alterations in the products of DNA expression such as RNA or protein that result from corresponding mutations in the DNA. Mutants may also be interchangeably called variants. The concept of a mutant includes any change in DNA sequence specific to the tumor cell (not present in DNA prepared from normal, non-neoplastic tissues).

B. FGFR Inhibitors and Mutations Leading to Inhibitor Resistance

A number of FGFR inhibitors are currently progressing through clinical trials. TKI258 (Dovitinib), a multitargeted receptor tyrosine kinase inhibitor has been shown to have considerable preclinical activity in cancer models with FGFR activation.

Targeted tyrosine kinase inhibitors (TKIs) have demonstrated dramatic clinical responses in the subset of patients whose tumors are 'addicted' to the oncogenic activity of the target kinase. However, the long-term efficacy of these agents is frequently limited by development of resistance to the targeted agent, often due to mutation of the target kinase or activation of alternative downstream or parallel signaling pathways. Identifying the mechanisms of resistance to targeted agents can aid the development of second-generation inhibitors and provide a mechanistic basis of combination with other molecularly targeted agents.

Resistance to TKIs often results from mutations within amino acid sequences that encode important structural features of the kinase. The kinase gatekeeper residue, which controls access to a hydrophobic pocket of the enzymatic active site, has been suggested to be a conserved hotspot of resistance formation. The most frequent site of clinically-detected drug resistant mutations is the gatekeeper residue of the target kinase (Table A). Mutation of the gatekeeper residue in FGFR1 to V561M results in resistance to the broadly active tyrosine kinase inhibitor PP58, suggesting mutation of this gatekeeper residue may function as a common mechanism of resistance to FGFR inhibitors.

TABLE A

Gatekeeper residues whose mutation has been clinically detected and associated with resistance to kinase inhibitors.

| Kinase | Gatekeeper Residue | | | | Drug-Resistant Gatekeeper Mutations | Tyrosine Kinase Inhibitor |
|---|---|---|---|---|---|---|
| C-KIT | V | I | T670 | E | Y | T670I | imatinib |
| c-ABL | I | I | 7315 | E | F | T315I | Imatinib, dasatinib |
| PDGFRA | I | I | T674 | E | Y | T674I | imatinib |
| EGFR | L | I | T790 | Q | L | T790M | gefitinib, erlotinib |
| FGFR1 | V | I | V561 | E | Y | na | |
| FGFR2b | V | I | V565 | E | Y | na | |

II. Methods of Identifying Candidates for Treatment with FGFR2 Inhibitors

A. Subject and Sample

A subject includes any human or non-human mammal, including for example: a primate, cow, horse, pig, sheep, goat, dog, cat, or rodent, capable of developing endometrial cancer including human patients that are suspected of having endometrial cancer, that have been diagnosed with endometrial cancer, or that have a family history of endometrial cancer. Methods of identifying subjects suspected of having endometrial cancer include but are not limited to: physical examination, family medical history, subject medical history, endometrial biopsy, or a number of imaging technologies such as ultrasonography, computed tomography, magnetic resonance imaging, magnetic resonance spectroscopy, or positron emission tomography. Methods of diagnosing endometrial cancer as well as the staging, grading, or other clinical delineation of endometrial cancer are well known to those of skill in the medical arts.

A sample may be a body fluid, such as serum, plasma, whole blood, urine, mucus, gastric juices, pancreatic juices, or lymph, from which free floating DNA, RNA, protein, peptide or fragments thereof may be detected and associated to tumor related mutations. Alternatively, a sample may be any cell source from which DNA, including genomic, somatic, and germline DNA may be obtained. In endometrial cancer, a biological sample is often obtained from the uterus and generally includes one or more endometrial tumor cells. Tumor cells may be obtained by any method now known in the art or yet to be disclosed, including for example, surgical resection, laser capture microdissection, isolation from blood or other fluids including lavage fluid, or any other method capable of obtaining and, if necessary, concentrating endometrial tumor cells.

The cell in a sample may be a tumor cell or a cancer cell for which growth may be slowed by the disclosed combination of pharmaceutical compositions either alone or in combination with another treatment modality, includes solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers for which growth may be slowed by the disclosed combination of pharmaceutical compositions include blood borne cancers such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

B. Detection of FGFR2 Variants

The presence of FGFR2 gene mutations in endometrial cancer strongly suggests that other human cancers may have similar mutations. When present in a cancer, mutant isoforms of FGFR2 represent a therapeutic target for tyrosine kinase inhibitors (TKIs), immunotherapy, and other novel targeted approaches, particularly to decrease risk of tumor metastasis. In cases where the resistance resulted from a FGFR2 mutation is incomplete, such that patients carrying such a mutation would respond to a higher dose of drug, the mutations variant of FGFR2 may be used to identify "high-dose responders." The selection of patients for therapy targeting variant FGFR2 isoforms to induce cancer cell death, reduce cancer growth, or decrease risk of metastasis would be optimized by pre-therapy analysis of cancer cells for the presence of FGFR2 gene mutations.

Analysis based on the presence of a FGFR2 variant can also be a type of test, assay, examination, result, readout, or interpretation that correlates with an increased or decreased probability that an individual has had, currently has, or will develop a particular disease, disorder, symptom, syndrome, or any condition related to health or bodily state. Examples of disease outcomes include, but need not be limited to, survival, death, progression of existing disease, remission of existing disease, initiation of onset of a disease in an otherwise disease-free subject, or the continued lack of disease in a subject in which there has been a remission of disease. Assessing the risk of a disease outcome also encompasses the concept of prognosis. A prognosis may be any assessment of the risk of disease outcome in an individual in which a particular disease has been diagnosed.

Alternatively, predicting a subject's response to a therapy, such as a drug therapy, based on the presence of a FGFR2 variant encompasses the concept of theranosis. Theranostic methods encompass detecting a mutation in the FGFR2 protein including mutations that result in increased activity of the FGFR2 protein. Examples of such mutations include mutations occurring in the junction between the immunoglobulin-like (Ig) domains II and III; mutations occurring in the IgIII domain; mutations occurring in the junction between the IgIII domain and the transmembrane (TM) domain; mutations occurring in the TM domain; mutations occurring in the junction between the TM domain and the tyrosine kinase domain I; mutations occurring in the tyrosine kinase domain I, or mutations occurring in the tyrosine kinase domain II. Such mutations may induce an amino acid substitution. Examples of such amino acid substitutions induced by mutations include but are not limited to: an S to W mutation at position 252, a P to R mutation at position 253, an S to C mutation at position 373, a Y to C mutation at position 376, a C to R mutation at position 383, an M to R mutation at position 392, a V to D mutation at position 396, an L to M mutation at position 398, an I to V mutation at position 548, an N to K mutation at position 550, an N to H mutation at position 550, and a K to E mutation at position 660 with position numbers as indicated in SEQ ID NO. 2. In one nonlimiting embodiment, the mutation consists of a deletion of nucleotide C and T at position 2290-91 of the nucleotide sequence (NM-02297.2) or an IVS10+2A>C splicing mutation with position numbers as indicated in SEQ ID. NO. 1 or any other somatic mutation found in an endometrial tumor cell.

Detection of FGFR2 variants can be based on PCR-based assays for these mutations, using for instance one or more of the following approaches: size fractionation by gel electrophoresis, direct sequencing, single-strand conformation polymorphism (SSCP), high pressure liquid chromatography (including partially denaturing HPLC), allele-specific hybridization, amplification refractory mutation screening, FGFR2 mutation screening by oligonucleotide microarray, restriction fragment polymorphism, MALDI-TOF mass spectrometry, or various related technologies (Abu-Duhier et al., Br. J. Haematol., 113: 983-988, 2001; Kottaridis et al., Blood, 98: 1752-1759, 2001; Choy et al., Ann. Hum. Gen., 63: 383-391, 1999; Grompe, Nature Genetics, 5: 111-117, 1993; Perlin & Szabady, Hum. Mutat., 19: 361-373, 2002; Amos & and Patnaik, Hum. Mutat., 19: 324-333, 2002; Cotton, Hum. Mutat., 19: 313-314, 2002; Stirewalt et al., Blood, 97: 3589-3595, 2001; Hung et al., Blood Coagul. Fibrinolysis, 13: 117-122, 2002; Larsen et al., Pharmacogenomics, 2: 387-399, 2001; Shchepinov et al., Nucleic Acids Res., 29: 3864-3872, 2001).

Mutated forms of FGFR2 nucleic acids, such as in FGFR2 DNA or any transcripts (including any splice variants now known or yet to be disclosed) as well as a deregulated expression (including overexpression or underexpression) of FGFR2 or other elements of a FGFR2 pathway may be detected by any of a variety of suitable methods.

Any method capable of detecting a mutated nucleic acid in a biological sample now known or yet to be disclosed may be employed and many strategies of genotypic analysis are now known to those skilled in the art. Some of these methods use nucleic acid sequences such as specific oligonucleotides to detect mutations in an FGFR2 nucleic acid in a biological sample. Such oligonucleotides may specifically hybridize to a nucleic acid sequence containing the specific mutation, or to a region adjacent to the site of mutation. Other methods use primers that permit amplification of all or part of an FGFR2 nucleic acid. Alternatively, or in combination with such techniques, oligonucleotide sequencing described herein or known to the skilled artisan may be applied to detect the FGFR2 mutations. One skilled in the art may use hybridization probes in solution and in embodiments employing solid-phase procedures. In such procedures, the test nucleic acid is adsorbed or otherwise affixed to a selected matrix or surface. The fixed, single-stranded nucleic acid is then subjected to specific hybridization with selected probes. Alternatively, one skilled in the art may use oligonucleotide primers in an amplification technique, such as PCR or reverse-PCR ("reverse polymerase chain reaction"), to specifically amplify a target DNA or mRNA, respectively. Such primers include primers that permit amplification of FGFR2 exons.

One example of such a method includes but is not limited to the following: contacting a biological sample containing DNA with specific oligonucleotides permitting the amplification of all or part of the FGFR2 gene, the DNA contained in the sample having been rendered accessible, where appropriate, to hybridization, and under conditions permitting a hybridization of the primers with the DNA contained in the biological sample; amplifying said DNA; detecting the amplification products; and comparing the amplified products obtained to the amplified products obtained with a normal control biological sample, and thereby detecting an abnormality in the FGFR2 gene if such abnormality is present and not detecting an abnormality if such abnormality is not present.

Alternatively, a sample may be sequenced directly with no amplification. In such methods, the sequenced DNA is compared to a normal genomic control sequence. The control sequence may be obtained from another subject or from a noncancerous sample from the same subject. One such method of sequencing is allele specific primer extension in which sample DNA hybridized to a chip is used as a synthesis template with the affixed oligonucleotide as a primer. Only the added dNTP's are labeled. Incorporation of the labeled dNTP then serves as a signal indicating the presence of the mutation. The fluorescent label may be detected by any of a number of instruments configured to read at least four different fluorescent labels on a DNA chip. In an alternative method, the identity of the final dNTP added to the oligonucleotide may be assessed by mass spectrometry. In this method, the dNTP's may, but need not, be labeled with a label of known molecular weight.

Other methods of detecting abnormalities in FGFR2 include those that detect abnormalities in the transcript of the FGFR2 gene. Such methods include amplifying mRNA transcripts in a biological sample by techniques such as RT-PCR (reverse transcription PCR). One example of such a method includes but is not limited to the following: producing cDNA from mRNA contained in a biological sample; contacting said cDNA with specific oligonucleotides capable of amplifying of all or part of the transcript of the FGFR2 gene, under conditions capable of hybridizing the primers with said cDNA; amplifying said cDNA; detecting the amplification products; comparing the amplified products obtained to the amplified products obtained with a normal control biological sample, and thereby detecting an abnormality in the transcript of the FGFR2 gene if such an abnormality is present and not detecting an abnormality if such an abnormality is not present. A control may be any noncancerous endometrial tissue control sample known as noncancerous to those skilled in the art, for example, a normal adjacent endometrium sample or a normal FGFR2 mRNA or DNA, obtained from blood, buccal swab or other source.

Additionally, RT-PCR allows visualization of the consequences of a splicing mutation such as exon skipping or aberrant splicing due to the activation of a cryptic site.

Nucleic acids that hybridize to mutant forms of FGFR2 may be used as probes in theranostic assays. Such a probe may comprise a substantially purified oligonucleotide that further includes a region having a nucleotide sequence that is capable of hybridizing specifically to a region of a FGFR2 gene that may be mutant or polymorphic. Such probes can then be used to detect specifically which, if any, mutation of the FGFR2 gene is present in a sample taken from a subject. The mutant or polymorphic region can be located in the promoter, exon, or intron sequences of the FGFR2 gene. In general, such probes have a sufficient number of nucleotides to allow specific hybridization to the target nucleotide sequence. Probes complementary to mutant sequences with the appropriate specificity may be constructed by those skilled in the art. For example, a portion of the FGFR2 gene may first be amplified and isolated from chromosomal DNA and hybridized to a probe. In such a case a probe of 10, 15, 20, 30, 50, or 100 nucleotides may be used.

The probe or primer may include a label. A label may be any substance capable of aiding a machine, detector, sensor, device, or enhanced or unenhanced human eye from differentiating a sequence that contains a particular allele from a sequence that does not contain the allele. Examples of labels include but are not limited to: a radioactive isotope or chelate thereof, a dye (fluorescent or nonfluorescent), stain, enzyme, or nonradioactive metal. Specific examples include but are not limited to: fluorescein, biotin, digoxigenin, alkaline phosphatase, biotin, streptavidin, $^3$H, $^{14}$C, $^{32}$P, $^{35}$S, or any other compound capable of emitting radiation, rhodamine, 4-(4'-dimethylamino-phenylazo)benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that signals the presence of bound ligand to an allele. In one embodiment of the invention, the label includes one or more dyes optimized for use in genotyping. Examples of such dyes include but are not limited to: dR110, 5-FAM, 6FAM, dR6G, JOE, HEX, VIC, TET, dTAMRA, TAMRA, NED, dROX, PET, and LIZ.

Alternatively, the probe may be modified to be more stable. Exemplary nucleic acid molecules that may be used to modify the probe to increase stability include phosphoramidate, phosphothioate and methylphosphonate analogs of DNA (see also, U.S. Pat. Nos. 5,176,996; 5,264,564; and 5,256,775).

One may use HPLC or denaturing HPLC (DHPLC) techniques to analyze the FGFR2 nucleic acids. DHPLC was developed when observing that, when HPLC analyses are carried out at a partially denaturing temperature, homoduplexes can be separated from heteroduplexes having the same base pair length (Hayward-Lester, et al., Genome Research, 1995, 5:494; Underhill, et al., Proc. Natl. Acad. Sci. USA, 1996, 93:193; Doris, et al., DHPLC Workshop, 1997, Stanford University). Thus, the use of DHPLC was applied to mutation detection (Underhill, et al., Genome Research, 1997, 7:996; Liu, et al., Nucleic Acid Res., 1998, 26; 1396). DHPLC can separate heteroduplexes that differ by as little as one base pair. "Matched Ion Polynucleotide Chromatography" (MIPC), or Denaturing "Matched Ion Polynucleotide Chromatography" (DMIPC) as described in U.S. Pat. No. 6,287,822 or 6,024,878, are additional separation methods.

Alternatively, one can use the DGGE method (Denaturing Gradient Gel Electrophoresis), or the SSCP method (Single Strand Conformation Polymorphism) for detecting an abnormality in the FGFR2 gene. DGGE is a method for resolving multiple DNA fragments of identical length on the basis of sequence differences as small as a single base pair change, using electrophoresis through a gel containing varying concentrations of denaturant (Guldberg et al., Nuc. Acids Res. 1994, 22:880). SSCP is a method for detecting sequence differences between two DNAs, comprising hybridization of the two species with subsequent mismatch detection by gel electrophoresis (Ravnik-Glavac et al., Hum. Mol. Genet. 1994, 3:801). "HOT cleavage", a method for detecting sequence differences between two DNAs, comprising hybridization of the two species with subsequent mismatch detection by chemical cleavage (Cotton, et al, Proc. Natl. Acad. Sci. USA 1988, 85:4397), can also be used.

Techniques using microarrays including microarrays that utilize high-throughput screening, may also be advantageously implemented to detect genetic abnormalities or assess gene expression. Gene expression may be that of the FGFR2 gene or the expression of another gene upstream or downstream in a pathway of which FGFR2 is a component or any other gene the expression of which correlates with FGFR2 expression. Microarrays may be designed so that the same set of identical oligonucleotides is attached to at least two selected discrete regions of the array, so that one can easily compare a normal sample, contacted with one of said selected regions of the array, against a test sample, contacted with another of said selected regions. These arrays use microfluidic conduits to avoid the mixture of normal sample and test sample. Examples of microarray techniques include those developed by Nanogen, Inc. (San Diego, Calif.) and those developed by Affymetrix (Santa Clara, Calif.). However, all types of microarrays, also called "gene chips" or "DNA chips", may be adapted for the identification of mutations. Such microarrays are well known in the art.

The solid support on which oligonucleotides are attached may be made from glass, silicon, plastic (e.g., polypropylene, nylon), polyacrylamide, nitrocellulose, or other materials now known or yet to be disclosed. One method for attaching the nucleic acids to a surface is by printing on glass plates, as is described generally by Schena et al., Science 1995, 270: 467-470. This method is especially useful for preparing microarrays of cDNA. See also, DeRisi et al., Nature Genetics 1996, 14:457-460; Shalon et al., Genome Res. 1996, 6:639645; and Schena et al., Proc. Natl. Acad. Sci. USA 1995, 93:10539-11286.

Other methods for making microarrays, e.g., by masking (Maskos and Southern, Nuc. Acids Res. 1992, 20:1679-1684), may also be used. In principal, any type of array, for example, dot blots on a nylon hybridization membrane (see Sambrook et al., Molecular Cloning A Laboratory Manual (2nd Ed.), Vol. 1-3, Cold Spring Harbor Laboratory, Cold Spring Harbor, N.Y., 1989) could be used, although, as will be recognized by those of skill in the art. For these assays nucleic acid hybridization and wash conditions are chosen so that the attached oligonucleotides specifically hybridize to at least a portion of the FGFR2 gene present in the tested sample sequence but does not hybridize to a site with a non-complementary nucleic acid sequence. The terms "hybridize" and "bind" are used interchangeably.

Alternatively, one may use allele specific hybridization to detect the mutant. In allele-specific hybridization, oligonucleotide sequences representing all possible variations at a polymorphic site are included on a DNA chip. The chip and sample are subject to conditions under which the labeled sample DNA will only bind to an oligonucleotide with an exact sequence match. In allele-specific primer extension, sample DNA hybridized to the chip may be used as a synthesis template with the affixed oligonucleotide as a primer. Under this method, only the added dNTP's are labeled. Incorporation of the labeled dNTP then serves as the signal indicating the presence of the allele. The fluorescent label may be detected by any of a number of instruments configured to read at least four different fluorescent labels on a DNA chip. In another alternative, the identity of the final dNTP added to the oligonucleotide may be assessed by mass spectrometry. In this alternative, the dNTP's may, but need not be labeled with a label of known molecular weight.

One polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g., Shalon et al, supra, and Chee et al., Science 1996, 274:610-614).

A variety of methods are available for detection and analysis of the hybridization events. Depending on the label used, detection and analysis may be carried out, for example fluorimetrically, colorimetrically or by autoradiography. By observing and measuring emitted radiation, such as fluorescent radiation or a particle emission, information may be obtained about the hybridization events. When fluorescently labeled probes are used, the fluorescence emissions at each site of transcript array can be detected by, for example, scanning confocal laser microscopy. In scanning confocal laser microscopy, a separate scan using the appropriate excitation line, is carried out for each of at least two fluorophores used to label probes. Alternatively, a laser that allows simultaneous specimen illumination at wavelengths specific to the two fluorophores and emissions from the two fluorophores may be used (see Shalon et aI. Genome Res. 1996, 6:639-695).

In addition, mutant or variant FGFR2 proteins may be detected through novel epitopes recognized by polyclonal and/or monoclonal antibodies used in ELISA, immunoblotting, flow cytometric, immunohistochemical and other mutant protein detection strategies (Wong et al., Cancer Res., 46: 6029-6033, 1986; Luwor et al., Cancer Res., 61: 5355-5361, 2001; Mishima et al., Cancer Res., 61: 5349-5354, 2001; Ijaz et al., J. Med. Virol., 63: 210-216, 2001). In ELISA assays, an antibody raised against whole FGFR2, or a fragment of FGFR2, or any mutant form of FGFR2 is immobilized onto a solid surface capable of binding proteins nonspecifically. Alternatively, purified FGFR2 or FGFR2 mutant, or any fragment thereof is immobilized onto the solid surface directly. Antibodies to be used in immunoassays that detect the presence of mutant forms of FGFR2 may be produced by any of a number of techniques that include, but are not limited to, the techniques below. Such antibodies include, but are not limited to, polyclonal, monoclonal, chimeric, single chain, Fab fragments, Fab expression library, humanized antibodies, or any functional fragments thereof.

Quantification of FGFR2 in the sample may then be achieved by measuring the degree of color generation using, for example, a visible spectra spectrophotometer. Examples of the enzyme to which the second antibody is conjugated include but are not limited to peroxidase and alkaline phosphatase. Examples of the substrate include a peroxidase substrate such as tetramethylbenzidine or any other substrate that changes the color or another property of a solution in response to the presence of a particular enzyme. The test protein concentration may be determined by comparison with a standard curve. These protocols are detailed in Current Protocols in Molecular Biology, V. 2 Ch. 11 and Antibodies, a Laboratory Manual, Ed Harlow, David Lane, Cold Spring Harbor Laboratory (1988) pp 579-593.

Other examples of immunoassays that may be used to detect mutant forms of FGFR2 protein include radioimmunoassay, sandwich immunoassays, immunoradiometric assays, gel diffusion precipitin reactions, immunodiffusion asays, in situ immuoassays or immunohistochemistry assays (IHC), precipitation reactions, agglutination assays, complement fixation assays, immunofluorescence assays, protein A assays, immunoelectrophoresis assays, flow cytometry based assays or any other technique now known or yet to be developed that utilizes a specific antibody to detect mutant FGFR2.

Additionally variant FGFR2 proteins could be detected by mass spectrometry assays coupled to immunoaffinity assays, the use of matrix-assisted laser desorption/ionization time-of-flight (MALDI-TOF) mass mapping and liquid chromatography/quadrupole time-of-flight electrospray ionization tandem mass spectrometry (LC/Q-TOF-ESI-MS/MS) sequence tag of tumor derived proteins separated by two-dimensional polyacrylamide gel electrophoresis (2D-PAGE) (Kiernan et al., Anal. Biochem., 301: 49-56, 2002; Poutanen et al., Mass Spectrom., 15: 1685-1692, 2001). All of these approaches may be used to detect a sequence anomaly or variant of the FGFR2 protein, a relative increase in the phosphorylation of the protein, or an increase in the inherent kinase activity of the protein.

C. Detection of Altered FGFR Activation

In addition to direct detection of variant FGFR2 proteins, it is expected that various FGFR2 variants will result in distinctive signal transduction profiles that could be detected by global gene expression profile or analysis of the activation or phosphorylation of various signaling intermediates (e.g., Stat3, Akt, ERK1/2, or S6K). For example, a FGFR2 receptor activation mutation may increase activation of the receptor by enhancing ligand binding, promoting altered or promiscuous ligand affinity with reduced selectivity, constitutive receptor dimerization, delayed degradation, impaired recycling from the cell membrane, overexpression, or kinase activation.

In one embodiment of the invention, the activity level of the FGFR2 variant protein in an endometrial cancer cell of a test subject may be assessed and compared to the activity in endometrial cells of a control subject. The increased activity of FGFR2 variant protein in the test subject compared to the control subject is indicative of drug resistance. The level of FGFR2 activity may be assessed by determining the level of activity in a FGFR2 signaling pathway through any method now known or yet to be developed. Examples include, but need not be limited to, assessing the expression of targets up- or down-regulated upon FGFR2 signaling, assessing the phosphorylation status of proteins phosphorylated or dephosphorylated on FGFR2 signaling, or any other method capable of detecting an increase in FGFR2 activity or ligand promiscuity.

It is believed that the nature and location of FGFR mutations affects the sensitivity of the resultant mutant protein to various TKIs. In some examples, a TKI may selectively inhibit wildtype FGFR2 protein, such that the TKI inhibits tyrosine kinase activity of a wildtype FGFR2 protein to a greater extent than it inhibits a variant FGFR2 protein. In some examples, the inhibitory effect of the compound is determined by direct assessment of tyrosine kinase activity. In additional examples, the inhibitory effect is determined by other assays, such as cell growth, apoptosis, or tumor metastasis assays, such as those described herein.

D. Detection of Altered Expression of FGFR2 Variants

Disclosed herein are methods of identifying subjects (such as a mammal, for example a human subject) for treatment with an inhibitor of FGFR2 to induce tumor cell death, inhibit tumor growth, or decrease risk of metastasis of a tumor cell, including determining altered expression of variant FGFR2 nucleic acid or protein in a sample from the subject (such as a blood or tissue sample, for example, a tumor biopsy). In particular examples, the variant includes a variant amino acid sequence at position(s) 536, 538, 548, 550, 565, 566, 618, 770 of SEQ ID NO: 2, or a combination of two or more thereof. In some examples, the subject has a variant FGFR2 that comprises a variant amino acid in the tyrosine kinase domain. In some examples, expression of the variant FGFR2 is compared to expression of FGFR2 in a normal control. In other examples, expression of the variant FGFR2 is compared to expression of FGFR2 in a cancer cell that does not express a variant FGFR2 molecule.

In particular examples, an increase in expression of a variant FGFR2 molecule relative to a control (such as FGFR2 expression in a cancer free tissue) indicates that the subject is a candidate for treatment with an inhibitor of that FGFR2 variant to induce tumor cell death, inhibit tumor growth, or decrease risk of metastasis of a tumor cell.

Such analysis can be based on PCR-based assays for these mutations, using for instance quantitative real-time PCR. See e.g. Bange et al., Cancer Res. 62:840-847, 2002. In some examples, primers and probes comprise at least 15 contiguous nucleotides of SEQ ID NO: 1.

In addition, overexpression of FGFR2 proteins may be detected through novel epitopes recognized by polyclonal and/or monoclonal antibodies used in ELISA, immunoblotting, flow cytometric, immunohistochemical and other mutant protein detection strategies (Wong et al., Cancer Res., 46: 6029-6033, 1986; Luwor et al., Cancer Res., 61: 5355-5361, 2001; Mishima et al., Cancer Res., 61: 5349-5354, 2001; Ijaz et al., J. Med. Virol., 63: 210-216, 2001)

III. Method for Screening FGFR2 Inhibitor

Disclosed herein are methods for identifying compounds that inhibit cancer, tumor growth or metastasis. The methods include contacting a test compound with a cell comprising FGFR2 polypeptide variant that increases risk of cancer. A compound that is an inhibitor of cancer may be identified by determining the effect of a test compound on activity of the FGFR2 polypeptide variant (including ligand binding or tyrosine kinase activity). In a particular example, a test compound that inhibits tyrosine kinase activity as compared to activity in the absence of the test compound identifies the test compound as an inhibitor of cancer. If the compound inhibits activity of a FGFR2 variant, it is further evaluated for its ability to inhibit cancer, tumor growth or metastasis.

The screening or creation, identification and selection of appropriate high affinity inhibitors of FGFR2 variants described herein can be accomplished by a variety of methods. One approach is to use structural knowledge about the target protein to design a candidate molecule with which it will precisely interact. An example would be computer assisted molecular design. A second approach is to use combinatorial or other libraries of molecules, whereby a large library of molecules is screened for affinity with regard to the target enzyme, or ability to inhibit activity of the target enzyme. In a further example, a panel of antibodies may be screened for ability to inhibit the target enzyme.

Cancer and precancer may be thought of as diseases that involve unregulated cell growth. Metastasis involves migration of tumor cells away from the site of the primary tumor, entry into the circulation, and proliferation at a new site. Cell growth involves a number of different factors. One factor is how rapidly cells proliferate, and another involves how rapidly cells die. Cells can die either by necrosis or apoptosis depending on the type of environmental stimuli. Cell motility is yet another factor that influences tumor growth kinetics and metastasis. Resolving which of the many aspects of cell growth a test compound affects can be important to the discovery of a relevant target for pharmaceutical therapy. Screening assays based on this technology can be combined with other tests to determine which compounds have growth inhibiting and pro-apoptotic activity.

A. Inhibitor Screening

Some embodiments provided herein involve determining the ability of a given compound to inhibit FGFR2 variants, for instance the ability to specifically inhibit constitutive kinase and/or metastasis promoting activities in the FGFR2 M536I, M538I, I548V, N550H, N550K, N550S, V565I, E566G, L618M, Y770IfsX14 variants described herein. Test compounds can be assessed for their probable ability to treat neoplastic lesions either directly, or indirectly by comparing their activities against compounds known to be useful for treating neoplasia. In particular, the compounds are tested for their ability to inhibit metastasis of a tumor that contains a FGFR2 variant that increases risk of metastasis.

B. Determining Tyrosine Kinase Influencing Activity

Compounds can be screened for inhibitory or other effects on the activity of the novel FGFR2 variants described herein using an expressed recombinant version of the enzyme, or a homolog or ortholog isolated from another species. Alternatively, cells expressing one of these FGFR2 polypeptides can be treated with a test compound and the effect of the test compound on phosphorylation of a specific target can be determined, for instance using one of the techniques described herein. In one example, tyrosine kinase activity is determined. Methods for determining tyrosine kinase phosphorylation influencing activity (e.g., inhibition) are known to one of skill in the art. In some examples, tyrosine kinase activity may be determined by assessing incorporation of a labeled phosphate (such as $P^{32}$-labeled phosphate) into a substrate which is capable of being phosphorylated by FGFR2 (such as a protein or a peptide fragment). In additional examples, tyrosine kinase activity may be determined by assessing FGFR2 autophosphorylation. In a further example, tyrosine kinase activity may be determined by assessing phosphorylation of downstream signaling components (such as Akt or MAP kinase). In additional examples, FGFR2 tyrosine kinase activity can be measured using a universal tyrosine kinase activity kit known in the art.

C. Determining Whether a Compound Reduces the Number of Tumor Cells

In an alternate embodiment, provided screening methods involve further determining whether the compound reduces the growth of tumor cells, for instance tumor cells known to express an activated tyrosine kinase mutation such as a mutation in FGFR2.

Various cell lines can be used, which may be selected based on the tissue to be tested. Certain cell lines are well characterized, and are used for instance by the United States National Cancer Institute (NCI) in their screening program for new anti-cancer drugs. Cell lines can also be constructed to express variant FGFR2 proteins.

Significant tumor cell growth inhibition, greater than about 30% at a dose of 100 μM or below, is further indicative that the compound is useful for treating neoplastic lesions. An $IC_{50}$ value may be determined and used for comparative purposes. This value is the concentration of drug needed to inhibit tumor cell growth by 50% relative to the control. In some embodiments, the $IC_{50}$ value is less than 100 μM in order for the compound to be considered further for potential use for treating, ameliorating, or preventing neoplastic lesions or tumor metastasis.

D. Determining Whether a Test Compound Induces Apoptosis

In other embodiments, screening methods provided herein further involve determining whether the test compound induces apoptosis in cultures of tumor or cancer cells.

Cancer cells include any cells derived from a tumor, neoplasm, cancer, precancer, cell line, or any other source of cells that are ultimately capable of potentially unlimited expansion and growth. Cancer cells may be derived from naturally occurring sources or may be artificially created. Cancer cells may also be capable of invasion into other tissues and metastasis when placed into an animal host. Cancer cells further encompass any malignant cells that have invaded other tissues and/or metastasized.

Expansion of a cancer cell includes any process that results in an increase in the number of individual cells derived from a cancer cell. Most commonly, expansion of a cancer cell results from mitotic division of the cancer cell whether in vitro or in vivo, though it may also include invasion and metastasis. The cancer cell may be in physical proximity to cancer cells from the same clone or from different clones that may or may not be genetically identical to it. Such aggregations may take the form of a colony, tumor or metastasis, any of which may occur in vivo or in vitro. Slowing the expansion of the cancer cell may be brought about either by inhibiting cellular processes that promote expansion or by bringing about cellular processes that inhibit expansion. Processes that inhibit expansion include processes that slow mitotic division and processes that promote cell senescence or cell death. Examples of specific processes that inhibit expansion include caspase dependent and independent pathways, autophagy, necrosis, apoptosis, and mitochondrial dependent and independent processes and further include any such processes yet to be discovered.

Two distinct forms of cell death may be described by morphological and biochemical criteria: necrosis and apoptosis. Necrosis is accompanied by increased permeability of the plasma membrane, whereby the cells swell and the plasma membrane ruptures within minutes. Apoptosis is characterized by membrane blebbing, condensation of cytoplasm, and the activation of endogenous endonucleases.

Apoptosis occurs naturally during normal tissue turnover and during embryonic development of organs and limbs. Apoptosis also can be induced by various stimuli, including cytotoxic T-lymphocytes and natural killer cells, by ionizing radiation and by certain chemotherapeutic drugs. Inappropriate regulation of apoptosis is thought to play an important role in many pathological conditions including cancer, AIDS, or Alzheimer's disease, etc.

Test compounds can be screened for induction of apoptosis, or cell death, using cultures of tumor cells maintained under conditions as described above. In some examples of such screening methods, treatment of cells with test compounds involves either pre- or post-confluent cultures and treatment for one to seven days at various concentrations of the test compounds. Apoptotic cells can be measured in both the attached and "floating" portions of the cultures. Both are collected by removing the supernatant, trypsinizing the attached cells, and combining both preparations following a centrifugation wash step (for example, 10 minutes, 2000 rpm).

Following treatment with a test compound, cultures can be assayed for apoptosis and necrosis, for instance by florescent microscopy following labeling with acridine orange and ethidium bromide. Many methods for measuring apoptotic cells are known to those of ordinary skill in the art; for instance, one method for measuring apoptotic cell number has been described by Duke & Cohen (Curr. Prot. Immuno., Coligan et al., eds., 3.17.1-3.17.1, 1992).

For example, floating and attached cells are collected by trypsinization and washed three times in PBS. Aliquots of cells are then centrifuged. The pellet is resuspended in media and a dye mixture containing acridine orange and ethidium bromide prepared in PBS and mixed gently. The mixture then can be placed on a microscope slide and examined for morphological features of apoptosis.

Apoptosis also can be quantified by measuring an increase in DNA fragmentation in cells that have been treated with test compounds. Commercial photometric enzyme immunoassays (EIA) for the quantitative in vitro determination of cytoplasmic histone-associated-DNA-fragments (mono- and oligo-nucleosomes) are available (e.g., Cell Death Detection ELISA, Boehringer Mannheim). The Boehringer Mannheim assay is based on a sandwich-enzyme-immunoassay principle, using mouse monoclonal antibodies directed against DNA and histones, respectively. This allows the specific determination of mono- and oligo-nucleosomes in the cytoplasmic fraction of cell lysates. According to the vendor, apoptosis is measured as follows: The sample (cell-lysate) is placed into a streptavidin-coated microtiter plate ("MTP"). Subsequently, a mixture of anti-histone-biotin and anti-DNA peroxidase conjugates is added and incubated for, for example, about two hours. During the incubation period, the anti-histone antibody binds to the histone-component of the nucleosomes and simultaneously fixes the immunocomplex to the streptavidin-coated MTP via its biotinylation. Additionally, the anti-DNA peroxidase antibody reacts with the DNA component of the nucleosomes. After removal of unbound antibodies by a washing step, the amount of nucleosomes is quantified by the peroxidase retained in the immunocomplex. Peroxidase is determined photometrically with ABTS7 (2,2'-Azido-[3-ethylbenzthiazolin-sulfonate]) as substrate.

Statistically significant increases of apoptosis (i.e., greater than 2 fold stimulation at a test compound concentration of 100 μM) are further indicative that the compound is useful for treating neoplastic lesions. Preferably, the $EC_{50}$ value for apoptotic activity should be less than 100 μM for the compound to be further considered for potential use for treating neoplastic lesions. $EC_{50}$ is understood herein to be the concentration that causes 50% induction of apoptosis relative to vehicle treatment.

E. Determining Whether a Compound Decreases Tumor Metastasis

In additional embodiments of the invention, screening methods provided herein further include determining whether the test compound decreases tumor metastasis, for example in an animal model of metastasis.

Methods for assessing tumor metastasis are known to one of skill in the art (see e.g. Khanna and Hunter, Carcinogenesis 26:513-523, 2005). One model of metastasis involves human-mouse xenografts, in which human cancer cell lines or tissues are transplanted into immunocompromised mice (such as SCID mice or nude mice). In similar methods, a cell line that has been engineered to express a molecule of interest (such as a FGFR2 variant polypeptide) is transplanted into an immunocompromised mouse. In one example, tumor cells or cell lines are injected directly into the systemic circulation. The site of injection largely defines the site to which metastases develop in these experimental systems. The most common site of tumor cell injection employed for experimental metastasis models is the lateral tail vein in mice, which results primarily in pulmonary metastases. In contrast, intrasplenic or portal vein injection of tumor cells is the most common site employed for developing metastasis in the liver and intracardiac injection of cells may result in metastases to several sites, including bone. Following injection of tumor cells or other cell lines into the circulation, development of metastases at the site of interest is monitored over a period of days or weeks.

Another model for assessing tumor metastasis utilizes orthotopic transplantation, wherein cancer cells are transplanted to the anatomic location or tissue from which a tumor was derived (for example by direct injection or surgical implantation of tumor fragments). Spontaneous metastases that arise from the orthotopic tumor can be assessed over a period of days or weeks.

The ability of a test compound to decrease or prevent tumor metastasis may be assessed by administering a test compound to an animal following injection of tumor cells subcutaneously, intramuscularly, or into the circulation or by orthotopic transplantation. The number, size, or time of development of metastases may be assessed. A compound that inhibits tumor metastasis may decrease the number of metastases, for example by at least 10%, 20%, 30%, 40%, 50%, 60%, 70% 80%, 90%, 95%, or even 100% as compared to a control sample. A compound that inhibits tumor metastasis may also decrease the size of metastases as compared to a control sample. Similarly, a compound that inhibits tumor metastasis may delay the onset of development of metastases, for example by at least one week, two weeks, one month, six months, one year, or even indefinitely.

IV. FGFR2 Inhibitors

The methods disclosed herein include identifying a subject as a candidate for treatment with an inhibitor of FGFR2 to induce tumor cell death, reduce tumor growth, or decrease risk of tumor metastasis. Inhibitors of growth factor receptors may be any agent including a pharmaceutically active ingredient or pharmaceutically acceptable salt thereof, a drug, a toxin, a chemical, a small organic molecule, a large molecule or peptide or an antibody.

A. Small Molecule Inhibitors

Some small molecule inhibitors may inhibit multiple growth factor receptors, while others may be specific for a particular family of growth factor receptor (for example, FGFRs), and still others may be specific for one growth factor receptor subtype (such as FGFR1, FGFR2, FGFR3, or FGFR4). In particular examples, a small molecule inhibitor specifically inhibits FGFR2 activity (such as TK activity). In still further examples, the small molecule inhibitor specifically inhibits one or more FGFR2 variants.

In some examples, the small molecule inhibitor of FGFR2 variants is a previously identified growth factor receptor or FGFR inhibitor, including TKI258 (4-amino-5-fluoro-3-[5-(4-methylpiperazin-1-yl)-1H-benzimidazol-2-yl]quinolin-2 (1H)-one, also known as CHIR-258); PD173074 (1-tert-butyl-3-[6-3,5-dimethoxyphenyl)-2-(4-diethylamino-butylamino)-pyrido[2,3-d]pyrimidin-7-yl]-urea; SU5402 (3-[3-(2-Carboxyethyl)-4-methylpyrrol-2-methylidenyl]-2-indolinone). Additional FGFR inhibitors may be identified utilizing the methods described herein. FGFR inhibitors include those that bind the active state of the receptor and those that bind the inactive state of the receptor.

In additional examples, inhibitors of FGFRs may include FGFR2-specific binding agents, such as polyclonal or monoclonal antibodies. Specific examples of FGFR2-specific binding agents are FGFR2-specific antibody or a functional fragment thereof, for instance monoclonal antibodies or fragments of monoclonal antibodies. Optionally, such monoclonal antibodies recognize an epitope of a variant FGFR2 (such as an epitope of a variant FGFR2 having an amino acid substitution in at least one position, including, but not limited to, amino acid(s) 536, 538, 548, 550, 550, 550, 565, 566, 618, 770 of SEQ ID NO: 2, or a combination thereof), and not (or to a lesser extent) an epitope of wild type FGFR2.

B. Large Molecules or Peptide Inhibitors

Large-molecule pharmaceuticals refer to pharmaceutical agents having a molecular weight greater than about 1000 daltons, e.g. peptidic drugs, vaccines and hormones. Many pharmaceutical agents are large molecules, for example, insulin, heparin, low molecular weight heparin (molecular weight less than about 5000 daltons), hirulog, hirugen, hirudin, interferons, cytokines, mono and polyclonal antibodies, immunoglobins, chemotherapeutic agents, vaccines, glycoproteins, bacterial toxins, hormones, calcitonins, glucagon like peptides (GLP-1), large molecular antibiotics (i.e., greater than about 1000 daltons), protein based thrombolytic compounds, platelet inhibitors, DNA, RNA, gene therapeutics, antisense oligonucleotides, opioids, narcotics, hypnotics, steroids and pain killers. When used herein, "dalton" means ¹⁄₁₂ the mass of the nucleus of carbon-12 (i.e. equivalent to 1.657.times.10.sup.-24 grams, also known as an "atomic mass unit"). Peptides are short polymers formed from the linking of amino acids and comprise, some of the basic components of human biological processes, including enzymes, hormones, and antibodies. The link between one amino acid residue and the next is known as a peptide bond or an amide bond. Proteins, by contrast, are typically much longer chains of amino acids, similarly linked by peptide bonds. Preferred pharmaceutical agents that may be inhibitors to FGFR2 and its variants include large molecule drugs of varying sizes.

C. Antibody Inhibitors

The term "antibody" is used herein in the broadest sense and refers generally to a molecule that contains at least one antigen binding site that immunospecifically binds to a particular antigen target of interest. Antibody thus includes but is not limited to native antibodies and variants thereof, fragments of native antibodies and variants thereof, peptibodies and variants thereof, and antibody mimetics that mimic the structure and/or function of an antibody or a specified fragment or portion thereof, including single chain antibodies and fragments thereof. The term thus includes full length antibodies and/or their variants as well as immunologically active fragments thereof, thus encompassing, antibody fragments capable of binding to a biological molecule (such as an antigen or receptor) or portions thereof, including but not limited to Fab, Fab', F(ab')2, facb, pFc', Fd, Fv or scFv (See, e.g., CURRENT PROTOCOLS IN IMMUNOLOGY, (Colligan et al., eds., John Wiley & Sons, Inc., NY, 1994-2001).

Monoclonal or polyclonal antibodies may be produced to either the normal FGFR2 protein or mutant forms of this protein, for instance particular portions that contain a mutation and therefore may provide a distinguishing epitope. Optimally, antibodies raised against these proteins or peptides would specifically detect the protein or peptide with which the antibodies are generated. That is, an antibody generated to the FGFR2 protein or a fragment thereof would recognize and bind the FGFR2 protein and would not substantially recognize or bind to other proteins found in human cells. In some embodiments, an antibody is specific for (or measurably preferentially binds to) an epitope in a variant protein versus the wild type protein, or vice versa, as discussed more fully herein.

D. Pharmaceutical Composition Comprising FGFR Inhibitor

Disclosed herein are methods of slowing the growth of cancer cells using pharmaceutical compositions comprising an FGFR inhibitor and/or derivatives thereof as an ingredient in a pharmaceutical composition to be used in combination with a test to determine whether the FGFR expressed by a tumor is susceptible to the composition. Such pharmaceutical compositions may take any physical form necessary depending on a number of factors including the desired method of administration and the physicochemical and stereochemical form taken by the compound or pharmaceutically acceptable salts of the compound. Such physical forms include a solid, liquid, gas, sol, gel, aerosol, or any other physical form now known or yet to be disclosed. The concept of a pharmaceutical composition containing the compound also encompasses an FGFR inhibitor, or a pharmaceutically acceptable salt thereof, or without any other additive. The physical form of the pharmaceutical composition may affect the route of administration and one skilled in the art would know to choose a route of administration that takes into consideration both the physical form of the compound and the disorder to be treated. Pharmaceutical compositions may be prepared using methodology well known in the pharmaceutical art. A pharmaceutical composition may include a second effective compound of a distinct chemical formula from the compound. This second effective compound may have the same or a similar molecular target as the target of the compound, or it may act upstream or downstream of the molecular target of the compound with regard to one or more biochemical pathways.

Pharmaceutical compositions include materials capable of modifying the physical form of a dosage unit. In one nonlimiting example, the composition includes a material that forms a coating that surrounds and/or contains the compound. Materials that may be used in such a coating, include, for example, sugar, shellac, gelatin, or any other inert coating agent.

Pharmaceutical compositions may be prepared as a gas or aerosol. Aerosols encompass a variety of systems including colloids and pressurized packages. Delivery of a composition in this form may include propulsion of a pharmaceutical composition containing the compound through use of liquefied gas or other compressed gas or by a suitable pump system. Aerosols may be delivered in single phase, bi-phasic, or tri-phasic systems.

In some aspects of the invention, the pharmaceutical composition is in the form of a solvate. Such solvates are produced by the dissolution of the compound in a pharmaceutically acceptable solvent. Pharmaceutically acceptable solvents include any mixtures of more than one solvent. Such solvents may include pyridine, chloroform, propan-1-ol, ethyl oleate, ethyl lactate, ethylene oxide, water, ethanol, and any other solvent that delivers a sufficient quantity of the compound to treat the affliction without serious complications arising from the use of the solvent in a majority of patients.

Pharmaceutical compositions may also include a pharmaceutically acceptable carrier. Carriers include any substance that may be administered with the compound with the intended purpose of facilitating, assisting, or helping the administration or other delivery of the compound. Carriers include any liquid, solid, semisolid, gel, aerosol or anything else that may be combined with the compound to aid in its administration. Examples include diluents, adjuvants, excipients, water, and oils (including petroleum, animal, vegetable or synthetic oils). Such carriers include particulates such as a tablet or powder, liquids such as an oral syrup or injectable liquid, and inhalable aerosols. Further examples include saline, gum acacia, gelatin, starch paste, talc, keratin, colloidal silica, and urea. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include polyethylene glycol, cyclodextrin, oils, or any other similar liquid carrier that may be formulated into a capsule. Still further examples of carriers include sterile diluents such as water, saline solution, physiological saline, Ringer's solution, isotonic sodium chloride, fixed oils such as synthetic mono or digylcerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents.

The pharmaceutical composition may take any of a number of formulations depending on the physicochemical form of the composition and the type of administration. Such forms include solutions, suspensions, emulsions, tablets, pills, pellets, capsules, capsules containing liquids, powders, sustained-release formulations, directed release formulations, lyophylates, suppositories, emulsions, aerosols, sprays, granules, powders, syrups, elixirs, or any other formulation now known or yet to be disclosed. Additional examples of suitable pharmaceutical carriers are described in "Remington's Pharmaceutical Sciences" by E. W. Martin, hereby incorporated by reference in its entirety.

Methods of administration include, but are not limited to, oral administration and parenteral administration. Parenteral administration includes, but is not limited to intradermal, intramuscular, intraperitoneal, intravenous, subcutaneous, intranasal, epidural, sublingual, intranasal, intracerebral, intraventricular, intrathecal, intravaginal, transdermal, rectally, by inhalation, or topically to the ears, nose, eyes, or skin. Other methods of administration include b ut are not limited to infusion techniques including infusion or bolus injection, by absorption through epithelial or mucocutaneous linings such as oral mucosa, rectal and intestinal mucosa. Compositions for parenteral administration may be enclosed in ampoule, a disposable syringe or a multiple-dose vial made of glass, plastic or other material.

Administration may be systemic or local. Local administration is administration of the compound to the area in need of treatment. Examples of local infusion during surgery; topical application, by local injection; by a catheter; by a suppository; or by an implant. Administration may be by direct injection at the site (or former site) of a cancer, tumor, or precancerous tissue or into the central nervous system by any suitable route, including intraventricular and intrathecal injection. Intraventricular injection can be facilitated by an intraventricular catheter, for example, attached to a reservoir, such as an Ommaya reservoir. Pulmonary administration may be achieved by any of a number of methods known in the art. Examples include use of an inhaler or nebulizer, formulation with an aerosolizing agent, or via perfusion in a fluorocarbon or synthetic pulmonary surfactant. The compound may be delivered in the context of a vesicle such as a liposome or any other natural or synthetic vesicle. Alternatively, the compound may be delivered by intrauterine devices similar to the Mirena® intrauterine system (Bayer Pharmaceuticals)

A pharmaceutical composition intended to be administered by injection may be prepared by dissolving the compound with water so as to form a solution. In addition, a surfactant may be added to facilitate the formation of a homogeneous solution or suspension. Surfactants include any complex capable of non-covalent interaction with the compound so as to facilitate dissolution or homogeneous suspension of the compound.

Pharmaceutical compositions may be prepared in a form that facilitates topical or transdermal administration. Such preparations may be in the form of a solution, emulsion, ointment, gel base, transdermal patch or iontophoresis device. Examples of bases used in such compositions include petrolatum, lanolin, polyethylene glycols, beeswax, mineral oil, diluents such as water and alcohol, and emulsifiers and stabilizers, thickening agents, or any other suitable base now known or yet to be disclosed.

Appropriate dosages for treatment with small organic molecules or antibodies can be determined by one of skill in the art. In general, an effective amount of a composition that includes a FGFR2 small molecule or antibody inhibitor administered to a subject will vary depending upon a number of factors associated with that subject, for example the overall health of the subject, the condition to be treated, or the severity of the condition. An effective amount of a composition that includes a FGFR2 inhibitor can be determined by varying the dosage of the compound and measuring the resulting therapeutic response, such as the decrease in metastasis of cancer, or the decrease in the size, volume or number of tumors. FGFR2 inhibitors can be administered in a single dose, or in several doses, as needed to obtain the desired response. However, the effective amount can be dependent on the source applied, the subject being treated, the severity and type of the condition being treated, and the manner of administration. In some examples, the dose of a FGFR2 inhibitor administered to a subject may be about 0.1 mg/kg to about 1000 mg/kg. In particular examples, the dose may be about 1 mg/kg to about 100 mg/kg, such as about 40 mg/kg.

In a further example, a therapeutically effective dose of a FGFR2 inhibitor includes daily use for at least about three months, such as at least about three months, about six months, about one year, about two years, about three years, about four years, or about five years.

Pharmaceutical compositions comprising an FGFR2 inhibitor can be administered alone, in the presence of a pharmaceutically acceptable carrier, in the presence of other therapeutic agents (for example other anti-cancer therapeutic agents), or both. Such anti-cancer therapeutics include, but are not limited to, chemotherapeutic drug treatment, radiation, gene therapy, hormonal manipulation, immunotherapy and antisense oligonucleotide therapy. Examples of useful chemotherapeutic drugs include, but are not limited to, hydroxyurea, busulphan, cisplatin, carboplatin, chlorambucil, melphalan, cyclophosphamide, Ifosphamide, danorubicin, doxorubicin, epirubicin, mitoxantrone, vincristine, vinblastine, Navelbine® (vinorelbine), etoposide, teniposide, paclitaxel, docetaxel, gemcitabine, cytosine, arabinoside, bleomycin, neocarcinostatin, suramin, taxol, mitomycin C, and the like. The compounds of the invention are also suitable for use with standard combination therapies employing two or more chemotherapeutic agents. It is to be understood that anti-cancer therapeutics for use in the present invention also include novel compounds or treatments developed in the future.

Further, addition of a pharmaceutical composition to cancer cells includes all actions by which a pharmaceutical composition is placed into sufficiently close proximity to a cancer cell that the effect of the pharmaceutical composition on the cancer cell is realized. The type of addition chosen will depend upon whether the cancer cells are in vivo, ex vivo, or in vitro, the physical or chemical properties of the pharmaceutical composition, and the effect the composition is to have on the cancer cell. Nonlimiting examples of addition include addition of a solution containing the pharmaceutical composition to tissue culture media in which in vitro cancer cells are growing; any method by which a pharmaceutical composition may be administered to an animal including intravenous, parenteral, or any other of the methods of administration; or the activation or inhibition of cells that in turn have effects on the cancer cells, such as immune cells like macophages and CD8+ T cells, or endothelial cells that may differentiate into blood vessel structures in the process of angiogenesis or vasculogenesis.

Cancer cells may display abnormal cell growth characterized as hyperplasia, metaplasia, or dysplasia, the presence of one or more characteristics of a transformed phenotype, or of a malignant phenotype, displayed in vivo or displayed in vitro by a cell sample derived from a patient can indicate the desirability of prophylactic/therapeutic administration of the composition of the invention. Such characteristics of a transformed phenotype include but not limited to morphology changes, looser substratum attachment, loss of contact inhibition, loss of anchorage dependence, protease release, increased sugar transport, decreased serum requirement, expression of fetal antigens. Further examples include leukoplakia (in which a benign-appearing hyperplastic or dysplastic lesion of the epithelium presents), or Bowen's disease (a carcinoma in situ), and are pre-neoplastic lesions indicative of the desirability of prophylactic intervention. In another example, fibrocystic disease (including cystic hyperplasia, mammary dysplasia, adenosis, or benign epithelial hyperplasia) is indicative of the desirability of prophylactic intervention.

Determination of an effective amount of the compound is within the capability of those skilled in the art, especially in light of the detailed disclosure provided herein. The effective amount of a pharmaceutical composition used to effect a particular purpose, as well as its toxicity, excretion, and overall tolerance may be determined in cell cultures or experimental animals by pharmaceutical and toxicological procedures either known now by those skilled in the art or by any similar method yet to be disclosed. One example is the determination of the $IC_{50}$ (half maximal inhibitory concentration) of the pharmaceutical composition in vitro in cell lines or target molecules. Another example is the determination of the $LD_{50}$ (lethal dose causing death in 50% of the tested animals) of the pharmaceutical composition in experimental animals. The exact techniques used in determining an effective amount will depend on factors such as the type, physical and/or chemical properties of the pharmaceutical composition, the property being tested, and whether the test is to be performed in vitro or in vivo. The determination of an effective amount of a pharmaceutical composition will be well known to one of skill in the art who will use data obtained from any tests in making that determination. Determination of an effective amount of compound for addition to a cancer cell also includes the determination of an effective therapeutic amount, including the formulation of an effective dose range for use in vivo, including in humans.

The effective amount of the pharmaceutical composition that results in the slowing of expansion of the cancer cells would preferably result in a concentration at or near the target tissue that is effective in slowing cellular expansion in neoplastic cells, but have minimal effects on non-neoplastic cells, including non-neoplastic cells exposed to radiation or recognized chemotherapeutic chemical agents. Concentrations that produce these effects can be determined using, for example, apoptosis markers such as the apoptotic index and/or caspase activities either in vitro or in vivo.

Pharmaceutical compositions may be administered prior to, concurrently with, or after administration of a second pharmaceutical composition. If the compositions are administered concurrently, they are administered within one minute of each other. If not administered concurrently, the second pharmaceutical composition may be administered a period of one or more minutes, hours, days, weeks, or months before or after the pharmaceutical composition that includes the compound.

Alternatively, a combination of pharmaceutical compositions may be cyclically administered. Cycling involves the administration of one or more pharmaceutical compositions for a period of time, followed by the administration of one or more different pharmaceutical compositions for a period of time and repeating this sequential administration, in order to reduce the development of resistance to one or more of the compositions, to avoid or reduce the side effects of one or more of the compositions, and/or to improve the efficacy of the treatment.

V. Kits

The invention further encompasses kits that facilitate the administration of the pharmaceutical compositions. An example of such a kit includes one or more units of effective amounts or dosages of the compositions. The unit dosage would be enclosed in a preferably sterile container and would be comprised of the compound and a pharmaceutically acceptable carrier. In another aspect, the unit dosage would comprise one or more lyophilates of the compound. In this aspect of the invention, the kit may include another preferably sterile container enclosing a solution capable of dissolving the lyophilate. However, such a solution need not be included in the kit and may be obtained separately from the lyophilate. In another aspect, the kit may include one or more devices used in administrating the unit dosages or a pharmaceutical composition to be used in combination with the compound. Examples of such devices include, but are not limited to, a syringe, a drip bag, a patch or an enema. In some aspects of the invention, the kit comprises the container that encloses the unit dosage.

The kit may further comprise one or more reagents used to identify a candidate for treatment with a pharmaceutical composition comprising one or more inhibitors to FGFR2 mutation variants. The reagents in the kit may be primers, probes, and/or antibodies that are capable of identifying a FGFR2 mutation variant.

The kit that facilitates nucleic acid based assays may further comprise one or more of the following: nucleic acid extraction reagents, controls, disposable cartridges, labeling reagents, enzymes including PCR amplification reagents such as the DNA polymerases Taq or Pfu, reverse transcriptase, or one or more other polymerases, and/or reagents that facilitate hybridization.

In another embodiment, the kit may further comprise a label that can be used to label the primer or probe oligonucleotide. A label may be any substance capable of aiding a machine, detector, sensor, device, or enhanced or unenhanced human eye from differentiating a sample that that displays positive expression from a sample that displays reduced expression. Examples of labels include but are not limited to: a radioactive isotope or chelate thereof, a dye (fluorescent or nonfluorescent), stain, enzyme, or nonradioactive metal. Specific examples include but are not limited to: fluorescein, biotin, digoxigenin, alkaline phosphatase, biotin, streptavidin, $^{3}H$, $^{14}C$, $^{32}P$, $^{35}S$, or any other compound capable of emitting radiation, rhodamine, 4-(4'-dimethylaminophenylazo) benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylene diamine tetra-acetic acid ("EDTA") and derivatives thereof or any other compound that signals the presence of the labeled nucleic acid. In one embodiment of the invention, the label includes one or more dyes optimized for use in genotyping. Examples of such dyes include but are not limited to: dR110, 5-FAM, 6FAM, dR6G, JOE, HEX, VIC, TET, dTAMRA, TAMRA, NED, dROX, PET, BHQ+, Gold540, and LIZ.

In yet another embodiment, the primers and probes in the kit may have been labeled, and can be applied without labeling process in PCR, sequencing reaction, or binding to a solid substrate such as oligonucleotide array.

The kit that facilitates the administration of the pharmaceutical compositions may also comprise instructions for use. In one embodiment, the kit may further comprise an indication that links the output of the assays provided by the kit to a particular result. For example, an indication may provide guide to associate the presence or absence of one or more sequences to a specific pharmaceutical composition. The output of the assay may be in a form of a particular sequence, a particular genotype, a particular $\Delta Ct$ level in a real-time quantitative PCR reaction, a level of fluorescence or radioactive decay, a value derived from a standard curve, or from a positive or negative control, or any combination of these and other outputs. The indication may be printed on a writing that may be included in the kit or it may be posted on the Internet or embedded in a software package. The writing may include graphical depictions of results such as a photomicrograph or amplification plot.

The kit that facilitates the administration of the pharmaceutical compositions may further comprise a device used to collect the sample. Such devices may include but need not be limited to: swabs, needles, blood collection tubes, wipes, or any other apparatus that may be used to collect a biological sample from a subject.

EXAMPLE

The following non-limiting examples are included to illustrate the invention.

Example 1

Mutations Identified in TKI258-Resistant BaF3.FGFR2b Clones

The BaF3 cell line is an IL-3 dependent murine pro-B cell line that is commonly employed to model TKI resistant mutations. BaF3 cells are made dependent on a specific oncogenic tyrosine kinase, and are cultured in the presence of a kinase inhibitor against that specific kinase, and resistant colonies can be screened for drug resistant mutations. This approach effectively reproduced the pattern and relative abundance of Bcr-Abl mutations seen clinically in imatinib-resistant patients (Von Bubnoff, N. et al, Blood. 2005 105:1652-1659)

The selected BaF3-FGFR2b cells were stably plated in 96 well plates at $1 \times 10^5$ and $4 \times 10^5$ cells/well. The growth media contains (−) IL3, 1 nM FGF10, 5 μg/ml heparin. TKI258 (Selleck Chemicals) was added at $IC_{50} \times 5$, ×10, ×15. Fresh 1 nM FGF10 with 5 μg/ml heparin were added 3 times per week. Colonies that grew out in the presence of TH1258 were selected and those selected colonies were expanded in the presence of 1 nM FGF10 and 5 μg/ml heparin. Of the $3 \times 10^8$ cells plated, 63 resistant clones were isolated.

Genomic DNA was isolated from the BaF3.FGFR2b colonies selected in the TKI258-resistance screen. Exons encoding the intracellular domain of FGFR2b were amplified and sequencing performed in two directions. Mutations in the intracellular domain of FGFR2b were identified in 26 of the 63 (41%) TKI258 resistant BaF3.FGFR2b clones. Among the 26 FGFR2b mutations, eleven different mutation variants were detected (Table 1). The eleven different mutation variants are: M536I, M538I, I548V, N550H, N550K, N550S, V565I, E566G, L618M, E719G, and Y770IfsX14. The most commonly mutated codon was N550, with mutations occurring in 19 of the 26 (73%) resistant clones. In addition, E719G mutation variant was identified in a clone with a N550H mutation; E719G mutation alone did not induce resistance to TKI258 or PD173074. There was an increase in mutation frequency with selective pressure, with an average of 20% mutation frequency in resistant clones selected at $5 \times IC_{50}$ and an average of 67% mutation frequency in resistant clones selected at $15 \times IC_{50}$.

TABLE 1

| TKI258 resistant FGFR2b variants: | |
|---|---|
| Mutation Identified | Mutation Incidence |
| M536I | 1 |
| M538I | 1 |
| I548V | 1 |
| N550H | 17 |

TABLE 1-continued

| TKI258 resistant FGFR2b variants: | |
|---|---|
| Mutation Identified | Mutation Incidence |
| N550K | 1 |
| N550S | 1 |
| V565I | 1 |
| E566G | 1 |
| L618M | 1 |
| E719G | 1 |
| Y770IfsX14 | 1 |

Example 2

BaF3/FGFR2b Mutants' Enhanced TKI Resistance and Receptor Activation Compared to Wildtype BaF3/FGFR2b wildtype and N550K mutation variant cells were plated at a density of 10,000 cells/well in a 96-well plate. TKI258 (Selleck Chemicals) or PD173074 (Calbiochem) was added in half-log dilutions in the absence of IL3 and in the presence of 1 nM FGF10 and 5 μg/mL heparin. After 72 hours, cell viability was measured using the ViaLight assay from Lonza (Visp, CH). The $IC_{50}$ values shown in FIG. 1 were normalized to DMSO control and data were analyzed with Prism software. The $IC_{50}$ value of TKI258 in BaF3/FGFR2b wildtype is 23.9 in comparison to 418.9 in N550K resistance cells, a nearly 20-fold difference. The $IC_{50}$ value of PD173074 in BaF3/FGFR2b wildtype is 4.5 in comparison to 775.6 in N550K resistance cells, over 170-fold difference.

Figure 2:
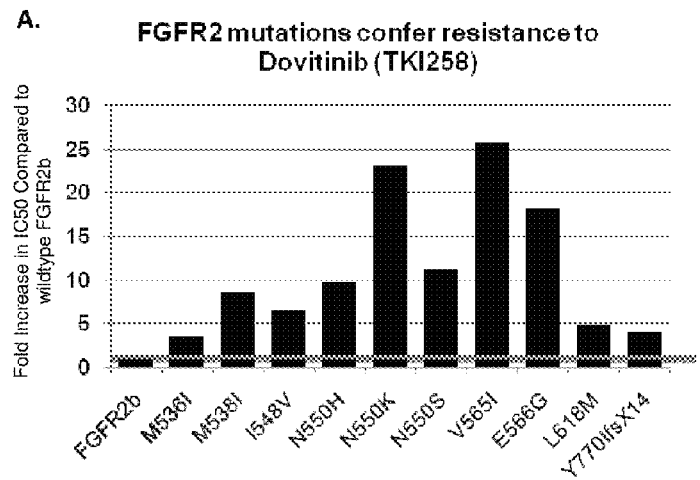
FIG. 2 depicts that the mutations result in resistance to TKI258 and PD173074 and that the mutations result in enhanced receptor activation in the presence of FGF ligand.
Figure 2:
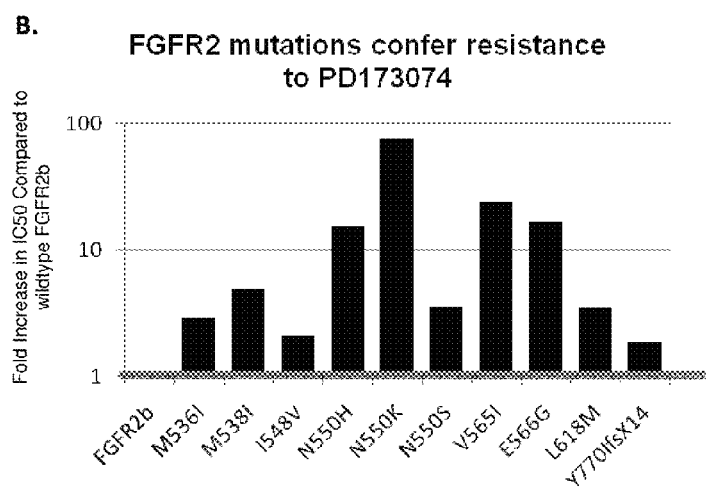
Figure 2:
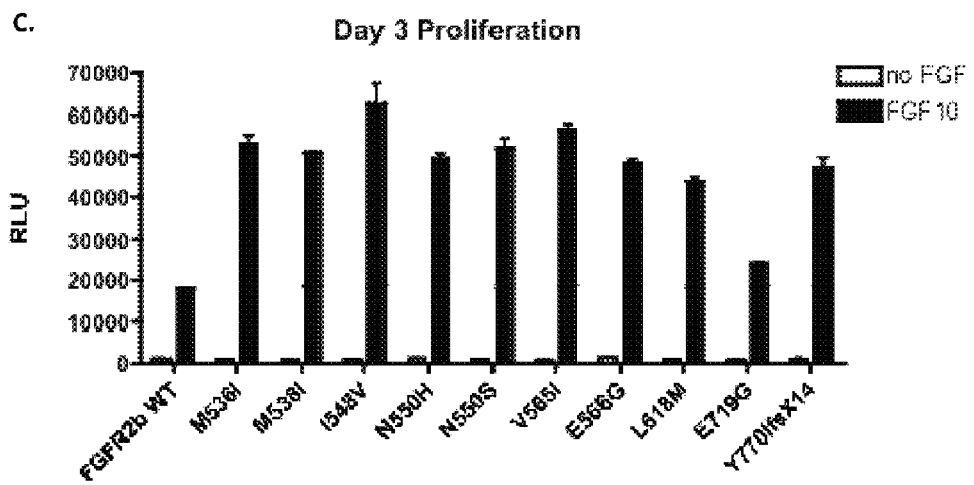

Similar tests were performed with the other 10 FGFR2b mutation variants. The majority of the mutations identified in this drug resistance screen result in activation of FGFR2. FIG. 2A showed the FGFR2 mutations confer resistance to TKI258 (Dovitinib). The fold increase in $IC_{50}$ compared to wildtype FGFR2 ranges from about 3-4 fold to about 25 fold, with V565I being the most resistant and M536I being the least resistant. The FGFR2 mutations resistance to another TKI PD173074 were also tested. In contrast to TKI285, the fold increase in $IC_{50}$ to PD173074 compared to wildtype FGFR2 is in a much wider range, as shown in FIG. 2B, with N550K being the most resistant and Y770IfsX14 being the least resistant to PD173074. The receptor activation of FGFR2 mutants and wildtype were measured and compared in the presence of FGF ligand. FIG. 2C shows the enhanced receptor activation of all FGFR2 mutant variants.

Example 3

Protein Structural Analysis of FGFR2b Mutation Variants

Mutation of gatekeeper residues is a common mechanism of resistance to kinase inhibitors observed clinically. However, there is only one gatekeeper residue (V565) mutation of FGFR2b identified in this BaF3 screen. In comparison, N550 is the most commonly mutated codon identified in this resistance screen. Most importantly, N550 is the second most common amino acid altered in endometrial cancer. This suggests that patients whose tumors possess mutations at N550 may be resistant to the anti-FGFR activity of TKI258.

Protein structural analyses were conducted to analyze the activation mechanism of FGFR2b mutation variants. These analyses provide structural insights to guide the development of next-generation inhibitors. It was found the activation was achieved mainly by two mechanisms: (A) disengaging the molecular break and (B) strengthening the hydrophobic spine.

Figure 3:
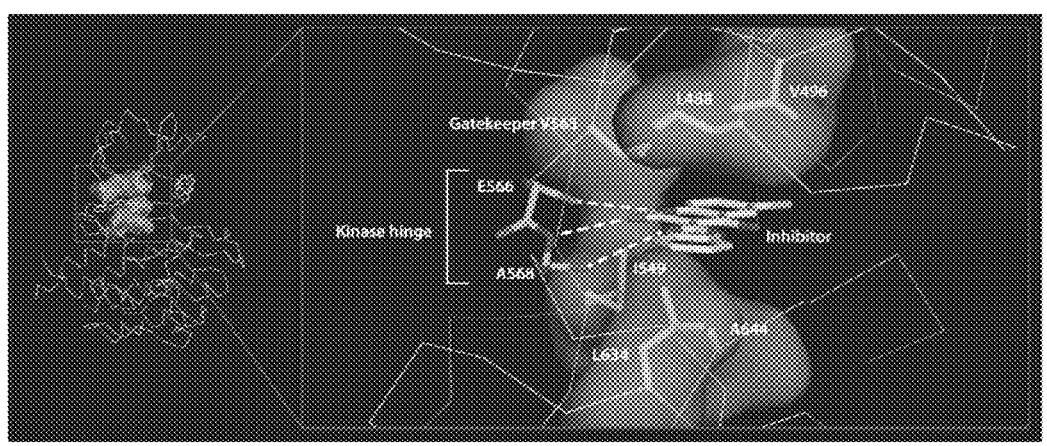
FIG. 3 depicts the predicted model for TKI258 interaction with the ATP binding pocket of the FGFR2b kinase. The binding of TKI258 to the FGFR2b kinase was modeled based on the binding of a compound with the same core to CHK-1 kinase.
Figure 4:
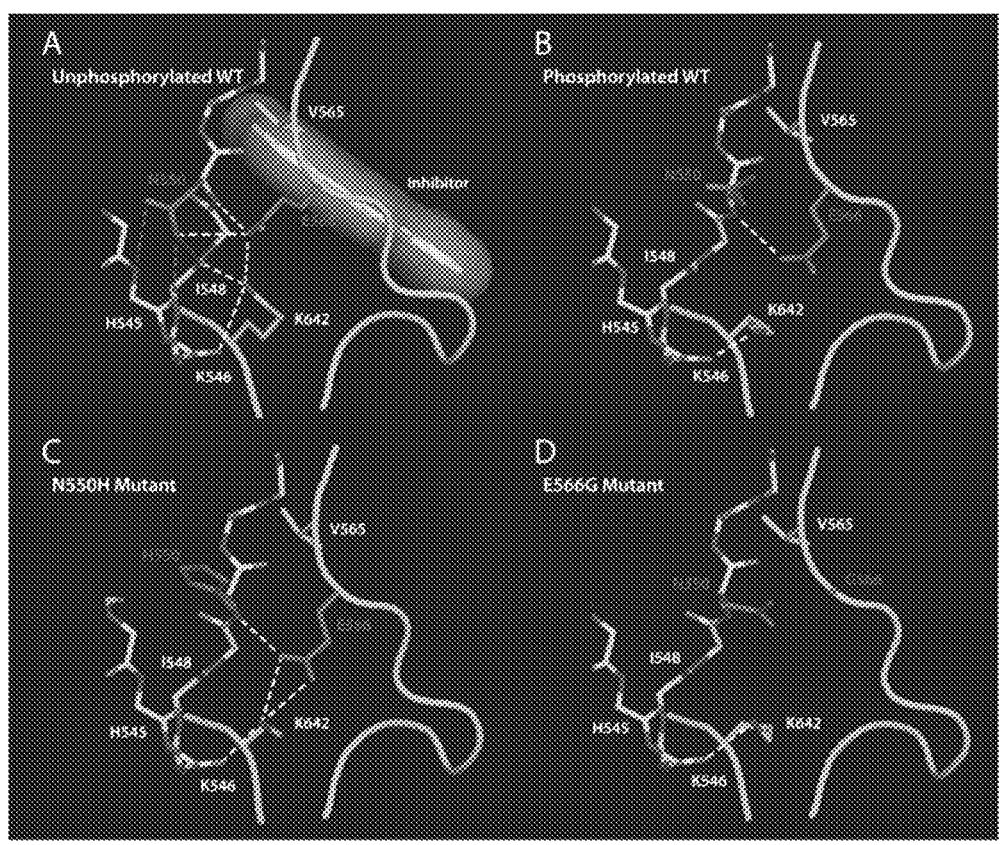
FIG. 4 depicts the drug resistance gain-of-function mutations at codons N550 and E566 in FGFR2b activate the kinase by breaking the molecular brake at the kinase hinge/interlobe region.

A. Disengaging the molecular break: The most commonly mutated residue identified in this resistance study was N550. FIG. 3 depicts the predicted model for TKI258 interaction with the ATP binding pocket of the FGFR2b kinase. The binding of TKI258 to the FGFR2b kinase was modeled based on the binding of a compound with the same core to CHK-1 kinase (Ni, Z. et al. Bioorg. Med. Chem. Lett. 2006 16 (12); 3121-24). N550, however, together with E566 and K642, forms part of a network of hydrogen bonds that act as a 'molecular brake' and keep the kinase in an autoinhibited state (FIG. 4A). Mutation of residues N550, E566 and/or K642 disengages this brake and relaxes the kinase towards its active state. FIG. 4B shows the active formation of the phosphorylated WT FGFR2. The N550H/K/S and E566G mutations identified in this study favor the active conformation of the kinase (FIG. 4C, 4D), thereby rendering the kinase resistant to TKI258.

B. Strengthening the hydrophobic spine: The 'hydrophobic spine' is a characteristic feature of the active state of several kinases. The hydrophobic spine is a network of hydrophobic interactions, and is stabilized by the gatekeeper substitution. For example, substitution of glycine for the residues constituting the spine disrupts the hydrophobic connectivity and inactivates the kinase. Furthermore, a small-molecule inhibitor that maximizes complementarity with the dismantled spine inhibits the gatekeeper mutation.

Figure 5:
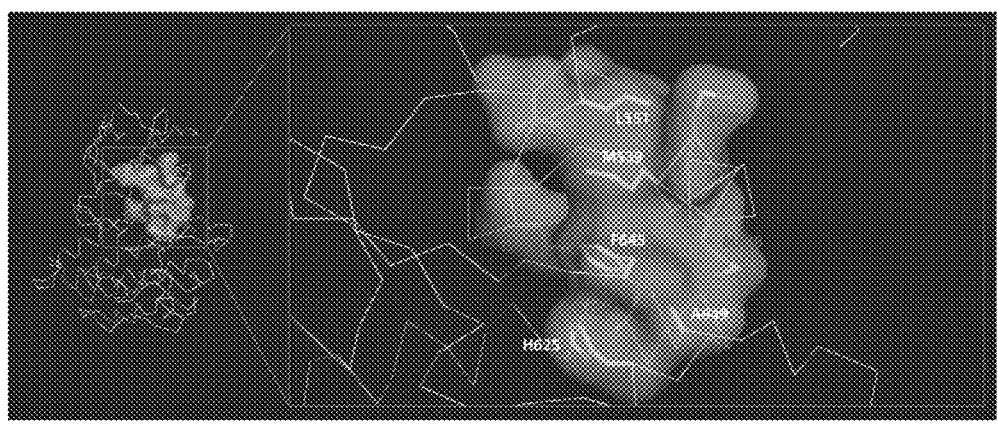
FIG. 5 depicts the drug resistance M536I, M538I, I548V, V565I and L618M mutations in FGFR2b lead to gain-of-function by strengthening the hydrophobic spine of the kinase.

The mutation variants M536I, M538I, I548V, V565I, and L618M, disclosed herein, likely activate the kinase by strengthening the hydrophobic spine (FIG. 5). This suggests that these mutations drive the kinase to the active state where the TKI258 inhibitor is not well recognized and bound, i.e. TKI258 predominantly binds to the inactive unphosphorylated form of the receptor.

Several of the resistance mutations (N550H/K/S, E566G) lead to receptor activation and TKI resistance by disengaging the molecular brake, and many of the remaining mutations (M536I, M538I, I548V, V565I, L618M) appear to induce resistance by strengthening the hydrophobic spine. These two mechanisms used by the FGFR2 mutant variants both drive the receptor to its active state, which often binds the receptor in its inactive state, and therefore, these FGFR2 mutation variants do not bind TKI258.

The foregoing description of a preferred embodiment and best mode of the invention known to the applicant at this time of filing the application has been presented and is intended for the purposes of illustration and description. It is not intended to be exhaustive or limit the invention to the precise form disclosed and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated. Therefore, it is intended that the invention not be limited to the particular embodiments disclosed for carrying out this invention, but that the invention will include all embodiments falling within the scope of the appended claims.

What is claimed is:

1. A method for identifying a tumor cell in a subject as susceptible or resistant to an inhibitor of fibroblast growth factor receptor (FGFR2) to induce tumor cell death, inhibit tumor growth, or decrease risk of metastasis of a tumor cell comprising:
   receiving a sample from the subject; and
   detecting the presence of at least one mutation variant of FGFR2 having the sequence of SEQ ID NO: 2, wherein the mutation variant is chosen from M536I, M538I, I548V, N550H, N550K, N550S , V565I, E566G, L618M, and Y770IfsX14 in the sample from the subject;
   determining the presence of the at least one mutation variant of FGFR2, wherein the presence of the at least one of the mutation variant of FGFR2 indicates that the tumor cell from the subject is resistant to the inhibitor; and
   treating the subject with the inhibitor wherein the at least one of the mutation variant of FGFR2 is determined to be absent from the sample.

2. The method of claim 1, wherein the sample comprises a tumor cell.

3. The method of claim 2, wherein the tumor cell is of a type dependent on FGFR activity.

4. The method of claim 1, wherein the sample is a body fluid comprising free floating tumor DNA, RNA, protein, peptide or fragments thereof.

5. The method of claim 1, wherein the at least one mutation variant of FGFR2 confers resistance to the tumor cell against the inhibitor chosen from TKI258 and PD173074.

6. The method of claim 1, wherein the presence of the at least one mutation variant of FGFR2 in the sample is determined by a technique chosen from PCR, RT-PCR, sequencing, hybridization, microarray genotyping, HPLC, Mass Spectrometry, and antibody-based immunoassays.

7. The method of claim 1, further comprising determining the sample has altered gene expression of the at least one FGFR2 variant relative to a control sample.

8. The method of claim 7, wherein the sample comprises a tumor cell.

9. The method of claim 8, wherein the tumor cell is of a type dependent on FGFR activity.

10. The method of claim 7, wherein FGFR variant gene expression is determined by quantitative real-time PCR, Western blotting, ELISA, or immunohistochemistry.

* * * * *

SEQUENCE LISTING

```
<160> NUMBER OF SEQ ID NOS: 2

<210> SEQ ID NO 1
<211> LENGTH: 4647
<212> TYPE: DNA
<213> ORGANISM: Homo sapiens
<220> FEATURE:
<221> NAME/KEY: misc_feature
<223> OTHER INFORMATION: fibroblast growth factor receptor 2 isoform 2
      precursor

<400> SEQUENCE: 1
ggcggcggct ggaggagagc gcggtggaga gccgagcggg cgggcggcgg gtgcggagcg      60
ggcgagggag cgcgcgcggc cgccacaaag ctcgggcgcc gcggggctgc atgcggcgta     120
cctggcccgg cgcggcgact gctctccggg ctggcggggg ccggccgcga gccccggggg     180
ccccgaggcc gcagcttgcc tgcgcgctct gagccttcgc aactcgcgag caaagtttgg     240
tggaggcaac gccaagcctg agtcctttct tcctctcgtt ccccaaatcc gagggcagcc     300
cgcgggcgtc atgcccgcgc tcctccgcag cctggggtac gcgtgaagcc cgggaggctt     360
ggcgccggcg aagacccaag gaccactctt ctgcgtttgg agttgctccc cgcaaccccg     420
ggctcgtcgc tttctccatc ccgacccacg cggggcgcgg gacaacaca ggtcgcggag     480 gagcgttgcc attcaagtga ctgcagcagc agcggcagcg cctcggttcc tgagcccacc     540
gcaggctgaa ggcattgcgc gtagtccatg cccgtagagg aagtgtgcag atgggattaa     600
cgtccacatg gagatatgga agaggaccgg ggattggtac cgtaaccatg gtcagctggg     660
gtcgtttcat ctgcctggtc gtggtcacca tggcaacctt gtccctggcc cggccctcct     720
tcagtttagt tgaggatacc acattagagc cagaagagcc accaaccaaa taccaaatct     780
```

```
ctcaaccaga agtgtacgtg gctgcgccag gggagtcgct agaggtgcgc tgcctgttga    840
aagatgccgc cgtgatcagt tggactaagg atggggtgca cttggggccc aacaatagga    900
cagtgcttat tggggagtac ttgcagataa agggcgccac gcctagagac tccggcctct    960
atgcttgtac tgccagtagg actgtagaca gtgaaacttg gtacttcatg gtgaatgtca   1020
cagatgccat ctcatccgga gatgatgagg atgacaccga tggtgcggaa gattttgtca   1080
gtgagaacag taacaacaag agagcaccat actggaccaa cacagaaaag atggaaaagc   1140
ggctccatgc tgtgcctgcg gccaacactg tcaagtttcg ctgcccagcc gggggaacc    1200
caatgccaac catgcggtgg ctgaaaaacg gaaggagtt taagcaggag catcgcattg   1260
gaggctacaa ggtacgaaac cagcactgga gcctcattat ggaaagtgtg gtcccatctg   1320
acaagggaaa ttatacctgt gtagtggaga atgaatacgg gtccatcaat cacacgtacc   1380
acctggatgt tgtggagcga tcgcctcacc ggcccatcct ccaagccgga ctgccggcaa   1440
atgcctccac agtggtcgga ggagacgtag agtttgtctg caaggtttac agtgatgccc   1500
agccccacat ccagtggatc aagcacgtgg aaaagaacgg cagtaaatac gggcccgacg   1560
ggctgcccta cctcaaggtt ctcaagcact cggggataaa tagttccaat gcagaagtgc   1620
tggctctgtt caatgtgacc gaggcggatg ctggggaata tatatgtaag gtctccaatt   1680
atatagggca ggccaaccag tctgcctggc tcactgtcct gccaaaacag caagcgcctg   1740
gaagagaaaa ggagattaca gcttccccag actacctgga gatagccatt tactgcatag   1800
gggtcttctt aatcgcctgt atggtggtaa cagtcatcct gtgccgaatg aagaacacga   1860
ccaagaagcc agacttcagc agccagccgg ctgtgcacaa gctgaccaaa cgtatccccc   1920
tgcggagaca ggtaacagtt tcggctgagt ccagctcctc catgaactcc aacacccgc    1980
tggtgaggat aacaacacgc ctctcttcaa cggcagacac ccccatgctg cagggtgtct   2040
ccgagtatga acttccagag acccaaaat gggagtttcc aagagataag ctgacactgg    2100
gcaagcccct gggagaaggt tgcttttggc aagtggtcat ggcggaagca gtgggaattg   2160
acaaagacaa gcccaaggag gcggtcaccg tggccgtgaa gatgttgaaa gatgatgcca   2220
cagagaaaga cctttctgat ctggtgtcag agatggagat gatgaagatg attgggaaac   2280
acaagaatat cataaatctt cttggagcct gcacacagga tgggcctctc tatgtcatag   2340
ttgagtatgc ctctaaaggc aacctccgag aatacctccg agcccggagg ccacccggga   2400
tggagtactc ctatgacatt aaccgtgttc ctgaggagca gatgaccttc aaggacttgg   2460
tgtcatgcac ctaccagctg gccagaggca tggagtactt ggcttcccaa aaatgtattc   2520
atcgagattt agcagccaga atgttttggg taacagaaaa caatgtgatg aaaatagcag   2580
actttggact cgccagagat atcaacaata tagactatta caaaaagacc accaatgggc   2640
ggcttccagt caagtggatg gctccagaag ccctgtttga tagagtatac actcatcaga   2700
gtgatgtctg gtccttcggg gtgttaatgt gggagatctt cactttaggg gctcgccct    2760
acccagggat tcccgtggag gaactttta agctgctgaa ggaggacac agaatggata    2820
agccagccaa ctgcaccaac gaactgtaca tgatgatgag ggactgttgg catgcagtgc   2880
cctcccagag accaacgttc aagcagttgg tagaagactt ggatcgaatt ctcactctca   2940
caaccaatga ggaatacttg gacctcagcc aacctctcga acagtattca cctagttacc   3000
ctgacacaag aagttcttgt tcttcaggag atgattctgt ttttctcca gaccccatgc   3060
cttacgaacc atgccttcct cagtatccac acataaacgg cagtgttaaa acatgaatga   3120
ctgtgtctgc ctgtccccaa acaggacagc actgggaacc tagctacact gagcagggag   3180
```

```
accatgcctc ccagagcttg ttgtctccac ttgtatatat ggatcagagg agtaaataat    3240
tggaaaagta atcagcatat gtgtaaagat ttatacagtt gaaaacttgt aatcttcccc    3300
aggaggagaa gaaggtttct ggagcagtgg actgccacaa gccaccatgt aaccctctc    3360
acctgccgtg cgtactggct gtggaccagt aggactcaag gtggacgtgc gttctgcctt    3420
ccttgttaat tttgtaataa ttggagaaga tttatgtcag cacacactta cagagcacaa    3480
atgcagtata taggtgctgg atgtatgtaa atatattcaa attatgtata aatatatatt    3540
atatatttac aaggagttat ttttgtatt gattttaaat ggatgtccca atgcacctag     3600
aaaattggtc tctctttttt taatagctat ttgctaaatg ctgttcttac acataatttc    3660
ttaattttca ccgagcagag gtggaaaaat acttttgctt tcagggaaaa tggtataacg    3720
ttaatttatt aataaattgg taatatacaa acaattaat catttatagt tttttttgta     3780
atttaagtgg catttctatg caggcagcac agcagactag ttaatctatt gcttggactt    3840
aactagttat cagatccttt gaaaagagaa tatttacaat atatgactaa tttggggaaa    3900
atgaagtttt gatttatttg tgtttaaatg ctgctgtcag acgattgttc ttagacctcc    3960
taaatgcccc atattaaaag aactcattca taggaaggtg tttcattttg gtgtgcaacc    4020
ctgtcattac gtcaacgcaa cgtctaactg gacttcccaa gataaatggt accagcgtcc    4080
tcttaaaaga tgccttaatc cattccttga ggacagacct tagttgaaat gatagcagaa    4140
tgtgcttctc tctggcagct ggccttctgc ttctgagttg cacattaatc agattagcct    4200
gtattctctt cagtgaattt tgataatggc ttccagactc tttggcgttg gagacgcctg    4260
ttaggatctt caagtcccat catagaaaat tgaaacacag agttgttctg ctgatagttt    4320
tggggatacg tccatctttt taagggattg ctttcatcta attctggcag gacctcacca    4380
aaagatccag cctcatacct acatcagaca aaatatcgcc gttgttcctt ctgtactaaa    4440
gtattgtgtt ttgctttgga aacacccact cactttgcaa tagccgtgca agatgaatgc    4500
agattacact gatcttatgt gttacaaaat tggagaaagt atttaataaa acctgttaat    4560
ttttatactg acaataaaaa tgtttctaca gatattaatg ttaacaagac aaaataaatg    4620
tcacgcaact taaaaaaaaa aaaaaaa                                        4647
```

<210> SEQ ID NO 2
<211> LENGTH: 822
<212> TYPE: PRT
<213> ORGANISM: Homo sapiens
<220> FEATURE:
<221> NAME/KEY: MISC_FEATURE
<223> OTHER INFORMATION: fibroblast growth factor receptor 2 isoform 2
      precursor

<400> SEQUENCE: 2

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
```

```
                85                  90                  95
Ala Thr Pro Arg Asp Ser Gly Leu Tyr Ala Cys Thr Ala Ser Arg Thr
                100                 105                 110

Val Asp Ser Glu Thr Trp Tyr Phe Met Val Asn Val Thr Asp Ala Ile
            115                 120                 125

Ser Ser Gly Asp Asp Glu Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
                180                 185                 190

Lys Asn Gly Lys Glu Phe Lys Gln Glu His Arg Ile Gly Gly Tyr Lys
                195                 200                 205

Val Arg Asn Gln His Trp Ser Leu Ile Met Glu Ser Val Val Pro Ser
            210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
                260                 265                 270

Asp Val Glu Phe Val Cys Lys Val Tyr Ser Asp Ala Gln Pro His Ile
            275                 280                 285

Gln Trp Ile Lys His Val Glu Lys Asn Gly Ser Lys Tyr Gly Pro Asp
            290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
                340                 345                 350

Ala Trp Leu Thr Val Leu Pro Lys Gln Gln Ala Pro Gly Arg Glu Lys
            355                 360                 365

Glu Ile Thr Ala Ser Pro Asp Tyr Leu Glu Ile Ala Ile Tyr Cys Ile
            370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
            420                 425                 430

Ala Glu Ser Ser Ser Ser Met Asn Ser Asn Thr Pro Leu Val Arg Ile
            435                 440                 445

Thr Thr Arg Leu Ser Ser Thr Ala Asp Thr Pro Met Leu Ala Gly Val
    450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
            500                 505                 510
```

-continued

```
Val Thr Val Ala Val Lys Met Leu Lys Asp Asp Ala Thr Glu Lys Asp
            515                 520                 525
Leu Ser Asp Leu Val Ser Glu Met Glu Met Met Lys Met Ile Gly Lys
    530                 535                 540
His Lys Asn Ile Ile Asn Leu Leu Gly Ala Cys Thr Gln Asp Gly Pro
545                 550                 555                 560
Leu Tyr Val Ile Val Glu Tyr Ala Ser Lys Gly Asn Leu Arg Glu Tyr
                565                 570                 575
Leu Arg Ala Arg Arg Pro Pro Gly Met Glu Tyr Ser Tyr Asp Ile Asn
            580                 585                 590
Arg Val Pro Glu Glu Gln Met Thr Phe Lys Asp Leu Val Ser Cys Thr
            595                 600                 605
Tyr Gln Leu Ala Arg Gly Met Glu Tyr Leu Ala Ser Gln Lys Cys Ile
    610                 615                 620
His Arg Asp Leu Ala Ala Arg Asn Val Leu Val Thr Glu Asn Asn Val
625                 630                 635                 640
Met Lys Ile Ala Asp Phe Gly Leu Ala Arg Asp Ile Asn Asn Ile Asp
                645                 650                 655
Tyr Tyr Lys Lys Thr Thr Asn Gly Arg Leu Pro Val Lys Trp Met Ala
            660                 665                 670
Pro Glu Ala Leu Phe Asp Arg Val Tyr Thr His Gln Ser Asp Val Trp
            675                 680                 685
Ser Phe Gly Val Leu Met Trp Glu Ile Phe Thr Leu Gly Gly Ser Pro
    690                 695                 700
Tyr Pro Gly Ile Pro Val Glu Glu Leu Phe Lys Leu Leu Lys Glu Gly
705                 710                 715                 720
His Arg Met Asp Lys Pro Ala Asn Cys Thr Asn Glu Leu Tyr Met Met
                725                 730                 735
Met Arg Asp Cys Trp His Ala Val Pro Ser Gln Arg Pro Thr Phe Lys
            740                 745                 750
Gln Leu Val Glu Asp Leu Asp Arg Ile Leu Thr Leu Thr Thr Asn Glu
            755                 760                 765
Glu Tyr Leu Asp Leu Ser Gln Pro Leu Glu Gln Tyr Ser Pro Ser Tyr
    770                 775                 780
Pro Asp Thr Arg Ser Ser Cys Ser Ser Gly Asp Asp Ser Val Phe Ser
785                 790                 795                 800
Pro Asp Pro Met Pro Tyr Glu Pro Cys Leu Pro Gln Tyr Pro His Ile
                805                 810                 815
Asn Gly Ser Val Lys Thr
            820
```